United States Patent
Yazaki et al.

(10) Patent No.: US 12,178,887 B2
(45) Date of Patent: *Dec. 31, 2024

(54) NIR-CONJUGATED TUMOR-SPECIFIC ANTIBODIES AND USES THEREOF

(71) Applicants: CITY OF HOPE, Duarte, CA (US); THE REGENTS OF THE UNIVERSITY OF CALIFORNIA, Oakland, CA (US)

(72) Inventors: Paul Yazaki, Duarte, CA (US); Jack Shively, Duarte, CA (US); Michael Bouvet, La Jolla, CA (US); Jonathan Delong, La Jolla, CA (US); Yuman Fong, Duarte, CA (US)

(73) Assignees: CITY OF HOPE, Duarte, CA (US); THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/160,202

(22) Filed: Jan. 26, 2023

(65) Prior Publication Data
US 2023/0241253 A1    Aug. 3, 2023

Related U.S. Application Data

(63) Continuation of application No. 16/993,950, filed on Aug. 14, 2020, now abandoned, which is a continuation of application No. 15/880,454, filed on Jan. 25, 2018, now Pat. No. 10,758,632.

(60) Provisional application No. 62/455,401, filed on Feb. 6, 2017.

(51) Int. Cl.
| | |
|---|---|
| *A61K 49/00* | (2006.01) |
| *A61B 5/00* | (2006.01) |
| *A61B 6/03* | (2006.01) |
| *A61B 6/40* | (2024.01) |
| *A61B 34/20* | (2016.01) |
| *A61K 39/00* | (2006.01) |
| *A61K 51/10* | (2006.01) |
| *C07K 16/30* | (2006.01) |

(52) U.S. Cl.
CPC ........ *A61K 49/0058* (2013.01); *A61B 5/0071* (2013.01); *A61B 6/4057* (2013.01); *A61B 34/20* (2016.02); *A61K 49/0002* (2013.01); *A61K 49/0032* (2013.01); *A61K 51/1048* (2013.01); *A61K 51/1057* (2013.01); *A61K 51/1063* (2013.01); *C07K 16/3007* (2013.01); *A61B 6/037* (2013.01); *A61B 2034/2055* (2016.02); *A61B 2505/05* (2013.01); *A61K 2039/505* (2013.01); *C07K 2317/24* (2013.01)

(58) Field of Classification Search
CPC ............ G01N 33/57492; G01N 33/534; A61B 6/037; C07K 14/4703
See application file for complete search history.

(56) References Cited

U.S. PATENT DOCUMENTS

| | | |
|---|---|---|
| 7,273,608 B2 | 9/2007 | Yazaki et al. |
| 7,776,330 B2 | 8/2010 | Yazaki et al. |
| 2009/0162278 A1 | 6/2009 | Ravn et al. |
| 2009/0234225 A1 | 9/2009 | Martin et al. |
| 2014/0120119 A1 | 5/2014 | Kobayashi et al. |
| 2016/0199524 A1* | 7/2016 | Hernandez ............. C07K 16/44 424/1.49 |

FOREIGN PATENT DOCUMENTS

WO    2015/042529 A2    3/2015

OTHER PUBLICATIONS

Zhang et al., Beyond the margins: real-time detection of cancer using targeted fluorophores, Nature Reviews Clinical Oncology, vol. 14, 347-364, Publication Date: Jan. 17, 2017 (Year: 2017).*
Abeam, "Goat Anti-Mouse IgG H&L (IRDye 800CW) Preadsorbed (ab216772)," retrieved from: IRDye® 800CW Goat Anti-Mouse (IgG) secondary antibody cross-adsorbed (ab216772) (abeam.com) (2022).
Adams, K. E., et al., "Comparison of Visible and Near-Infrared Wavelength-Excitable Fluorescent Dyes for Molecular Imaging of Cancer," J. Biomed. Optics 12(2):024017 (2007).
Alhanafy, A. M., et al., "Prognostic Factors for Hormone Sensitive Metastatic Prostate Cancer: Impact of Disease Volume," Asian Pac. J. Cancer Prev. 19(4):1113-1118 (2018).
An, Z., et al., "Development of a High Metastatic Orthotopic Model of Human Renal Cell Carcinoma in Nude Mice: Benefits of Fragment Implantation Compared to Cell-Suspension Injection," Clin. Exp. Metastasis 17:265-270 (1999).
Behr, T. M., et al., "Radioimmunotherapy of Small-Volume Disease of Metastatic Colorectal Cancer," Cancer 94(4 Suppl):1373-1381 (2002).
Behr, T. M., et al., "Radioimmunotherapy of Small Volume Disease of Colorectal Cancer Metastatic to the Liver: Preclinical Evaluation in Comparison to Standard Chemotherapy and Initial Results of a Phase I Clinical Study," Clin. Cancer Res. 5:3232s-3242s (1999 Suppl).
Boni, L., et al., "Clinical Applications of Indocyanine Green (ICG) Enhanced Fluorescence in Laparoscopic Surgery," Surg. Endosc. 29:2046-2055 (2015).
Bouvet, M., et al., "Glowing Tumors Make for Better Detection and Resection," Sci. Transl. Med. 3(110):110fs10 (2011).
Cao, H. S. T., et al., "Tumor-Specific Fluorescent Antibody Imaging Enables Accurate Staging Laparoscopy in an Orthotopic Model of Pancreatic Cancer," Hepatogastroenterology 59(118):1994-1999 (2012).

(Continued)

*Primary Examiner* — Peter J Reddig
*Assistant Examiner* — Cheng Lu
(74) *Attorney, Agent, or Firm* — Perkins Coie LLP; Lara J. Dueppen; Adeh Vartanian

(57) ABSTRACT

Disclosed is a tumor-specific antibody and fluorophore conjugate for detecting, localizing and imaging of various tumors. Also disclosed are methods for detecting, localizing and imaging a solid tumor before or during a tumor resection surgery using the antibody-fluorophore conjugate.

6 Claims, 18 Drawing Sheets
(17 of 18 Drawing Sheet(s) Filed in Color)

(56) References Cited

OTHER PUBLICATIONS

Cibula, D., et al., Bilateral Ultrastaging of Sentinel Lymph Node in Cervical Cancer: Lowering the False-Negative Rate and Improving the Detection of Micrometastasis; Esgyon (3):462-466 (2012).

Delong, J., et al., "Current Status and Future Perspectives of Fluorescence-Guided Surgery for Cancer," Expert Rev. Anticancer Ther. 16(1):71-81 (2016).

Dsouza, A. V., et al., "Review of Fluorescence Guided Surgery Systems: Identification of Key Performance Capabilities Beyond Indocyanine Green Imaging," J. Biomed. Opt. 21(8):080901 (2016).

Fu, X., et al., "Models of Human Metastatic Colon Cancer in Nude Mice Orthotopically Constructed by Using Histologically Intact Patient Specimens," Proc. Natl. Acad. Sci. USA 88:9345-9349 (1991).

Fu, X., et al., "Extensive Liver Metastasis from Human Colon Cancer in Nude and Scid Mice After Orthotopic Onplantation of Histologically-Intact Human Colon Carcinoma Tissue," Anticancer Res. 12:1395-1398 (1992).

Fu, X., et al., "A Metastatic Nude-Mouse Model of Human Pancreatic Cancer Constructed Orthotopically with Histologically Intact Patient Specimens," Proc. Natl. Acad. Sci. USA 89:5645-5649 (1992).

Furukawa, T., et al., "Nude Mouse Metastatic Models of Human Stomach Cancer Constructed Using Orthotopic Implantation of Histologically Intact Tissue," Cancer Res. 53:1204-1208 (1993).

Girgis, M. D., et al., "Targeting CEA in Pancreas Cancer Xenografts with a Mutated scFv-Fc Antibody Fragment," EJNMMI Research 1:24 (2011).

Harlaar, N. J., et al., "Molecular Fluorescence-Guided Surgery of Peritoneal Carcinomatosis of Colorectal Origin: A Single-Centre Feasibility Study," Cancer Gastroenterol. Hepatol. 1:283-290 (2016).

Hiroshima, Y., et al., "Successful Fluorescence-Guided Surgery on Human Colon Cancer Patient-Derived Orthotopic Xenograft Mouse Models Using a Fluorophore-Conjugated Anti-CEA Antibody and a Portable Imaging System," J. Laparoendoscopic Adv. Surg. Tech. 24(4):241-247 (2014).

Hiroshima, Y., et al., "Effective Fluorescence-Guided Surgery of Liver Metastasis Using a Fluorescent Anti-CEA Antibody," J. Surg. Oncol. 114(8):951-958 (2016).

Hoffman, R. M., et al., "Subcellular Imaging in the Live Mouse," Nat. Protoc. 1(2):775-782 (2006).

Kaushal, S., et al., Fluorophore-Conjugated Anti-CEA Antibody for the Intraoperative Imaging of Pancreatic and Colorectal Cancer, J. Gastrointest. Surg. 12(11):1938-1950 (2008).

Kitamura, T., et al., "Specificity of Lectin-Immobilized Fluorescent Nanospheres for Colorectal Tumors in a Mouse Model Which More Resembles the Clinical Disease," Contrast Media Mol. Imaging 10(2):135-143 (2015).

Li-Cor downloaded from: https://www.licor.com on Oct. 27, 2022 (Year: 2022).

Maawy, A. A., et al., "Comparison of a Chimeric Anti-Carcinoembryonic Antigen Antibody Conjugated with Visible or Near-Infrared Fluorescent Dyes for Imaging Pancreatic Cancer in Orthotopic Nude Mouse Models," J. Biomed. Opt. 18(12):126016 (2013).

Maawy, A. A., et al., "Specific Tumor Labeling Enhanced by Polyethylene Glycol Linkage of Near Infrared Dyes Conjugated to a Chimeric Anti-Carcinoembryonic Antigen Antibody in a Nude Mouse Model of Human Pancreatic Cancer," J. Biomed. Opt. 19(10):101504 (2014).

Maawy, A. A., et al., "Near Infra-Red Photoimmunotherapy with Anti-CEA-IR700 Results in Extensive Tumor Lysis and a Significant Decrease in Tumor Burden in Orthotopic Mouse Models of Pancreatic Cancer," PLoS One 10(3):e0121989 (2015).

Markov, P., et al., "Redefining the R1 Resection in Patients with Pancreatic Ductal Adenocarcinoma," J. Hepatobiliary Pancreat. Sci. 23:523-532 (2016).

Metildi, C. A., et al., "An LED Light Source and Novel Fluorophore Combinations Improve Fluorescence Laparoscopic Detection of Metastatic Pancreatic Cancer in Orthotopic Mouse Models," J. Am. Coll. Surg. 214(6):997-1007 (2012).

Metildi, C. A., et al., "Fluorescence-Guided Surgery and Fluorescence Laparoscopy for Gastrointestinal Cancers in Clinically-Relevant Mouse Models," Gastroenterol. Res. Pract. 2013:290634 (2013).

Metildi, C. A., et al., "Fluorescence-Guided Surgery of Human Colon Cancer Increases Complete Resection Resulting in Cures in an Orthotopic Nude Mouse Model," J. Surg. Res. 179(1):87-93 (2013).

Metildi, C. A., et al., "Fluorescence-Guided Surgery with a Fluorophore-Conjugated Antibody to Carcinoembryonic Antigen (CEA), that Highlights the Tumor, Improves Surgical Resection and Increases Survival in Orthotopic Mouse Models of Human Pancreatic Cancer," Ann. Surg. Oncol. 21(4):1405-1411 (2014).

Metildi, C. A., et al., "Fluorescently-Labeled Chimeric Anti-CEA Antibody Improves Detection and Resection of Human Colon Cancer in an Orthotopic Nude Mouse Model," J. Surg. Oncol. 109(5):451-458 (2014).

Moore, L. S., et al., "Characterizing the Utility and Limitations of Repurposing an Open-Field Optical Imaging Device for Fluorescence-Guided Surgery in Head and Neck Cancer Patients," J. Nucl. Med. 58(2):246-251 (2016).

Namikawa, T., et al., "Recent Advances in Near-Infrared Fluorescence-Guided Imaging Surgery Using Indocyanine Green," Surg. Today 45:1467-1474 (2015).

Nica, A., et al., "Does Small vol. Metastatic Lymph Node Disease Affect Long-Term Prognosis in Early Cervical Cancer?" Int. J. Gynecol. Cancer 30:285-290 (2019).

Pantel, K., et al., "Detection and Clinical Importance of Micrometastatic Disease," J. Natl. Cancer Inst. 91:1113-1124 (1999).

Rijpkema, M., et al., "SPECT- and Fluorescence Image-Guided Surgery Using a Dual-Labeled Carcinoembryonic Antigen-Targeting Antibody," J. Nucl. Med. 55:1519-1524 (2014).

Rosenthal, E. L., et al., "Safety and Tumor-specificity of Cetuximab-IRDye800 for Surgical Navigation in Head and Neck Cancer," Clin. Cancer Res. 21(16):3658-3666 (2015).

Rosenthal, E. L., et al., "Sensitivity and Specificity of Cetuximab-IRDye800CW to Identify Regional Metastatic Disease in Head and Neck Cancer," Clin. Cancer Res. 23(16):4744-4752 (2017).

Schwartz, G. F., et al., "Proceedings of the Consensus Conference on the Role of Sentinel Lymph Node Biopsy in Carcinoma of the Breast, Apr. 19-22, 2001, Philadelphia, Pennsylvania," Am. Cancer Soc. 2542-2551 (2002).

Strobel, O., et al., "Pancreatic Cancer Surgery: The New R-Status Counts," Ann. Surg. 265:565-573 (2017).

Van Driel, P. B. A. A., et al., "EpCAM as Multi-Tumour Target for Near-Infrared Fluorescence Guided Surgery," BMC Cancer 16:884 (2016).

Warram, J. M., et al., "Fluorescence-Guided Resection of Experimental Malignant Glioma Using Cetuximab-IRDye 800CW," Br. J. Neurosurg. 29(6):850-858 (2015).

Wong, J. Y.C., et al., "A Phase I Trial of 90Y-DOTA-Anti-CEA Chimeric T84.66 (cT84.66) Radioimmunotherapy in Patients with Metastatic CEA-Producing Malignancies," Cancer Biother. Radiopharm. 21(2):88-100 (2006).

Yazaki, P. J., et al., "Mammaliam Expression and Hollow Fiber Bioreactor Production of Recombinant Anti-CEA Diabody and Minibody for Clinical Applications," J. Immunol. Meth. 253:195-208 (2001).

Yazaki, P. J., et al., "Humanization of the Anti-CEA T84.66 Antibody Based on Crystal Structure Data," Prot. Eng. Des. Sel. 17(5):481-489 (2004).

Yazaki, P. J., et al., "A Series of Anti-CEA/Anti-DOTA Bispecific Antibody Formats Evaluated for Pre-Targeting: Comparison of Tumor Uptake and Blood Clearance," Prot. Eng. Des. Sel. 26(3):187-193 (2013).

Zhu, B., et al., "A Review of Performance of Near-Infrared Fluorescence Imaging Devices Used in Clinical Studies," Br. J. Radiol. 88:20140547 (2015).

(56) References Cited

OTHER PUBLICATIONS

Zhu, S., et al., "Near-Infrared-II Molecular Dyes for Cancer Imaging and Surgery," Adv. Mater. 31:1900321 (2019).

* cited by examiner

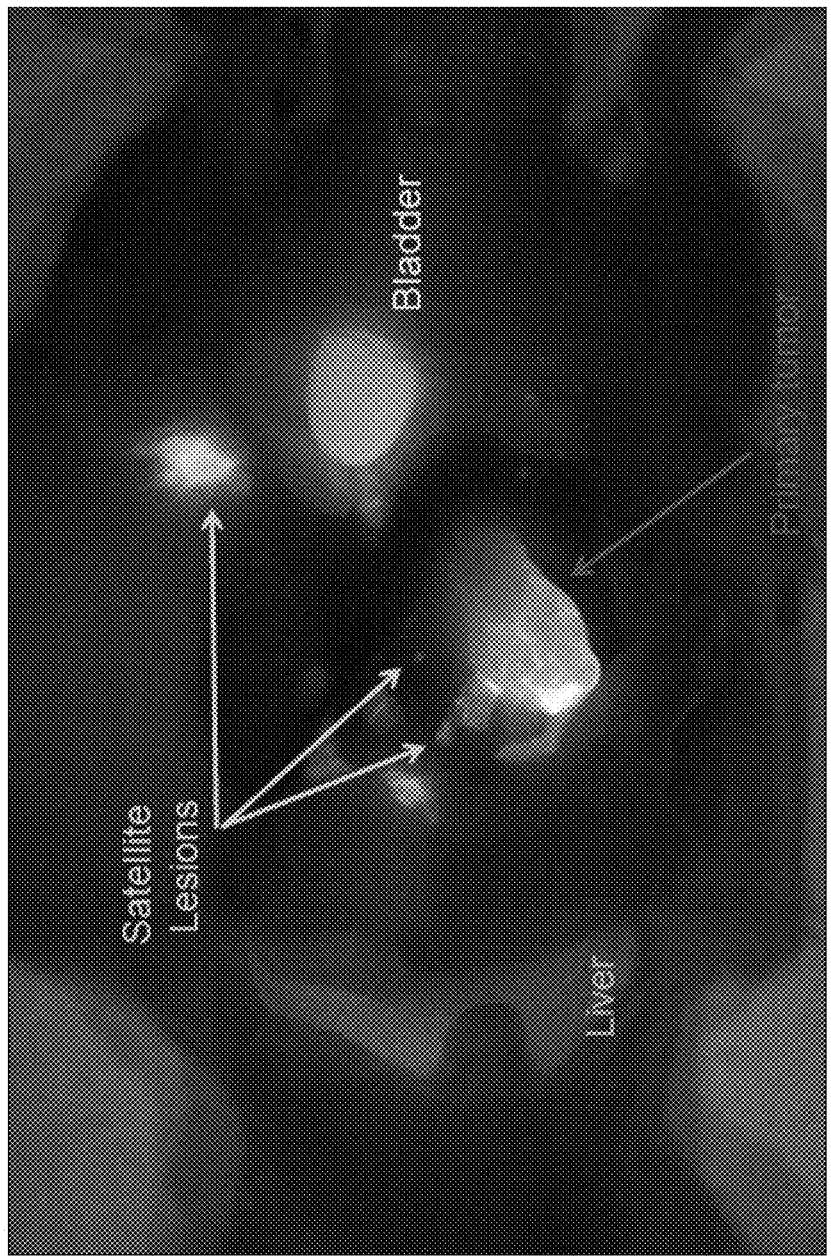

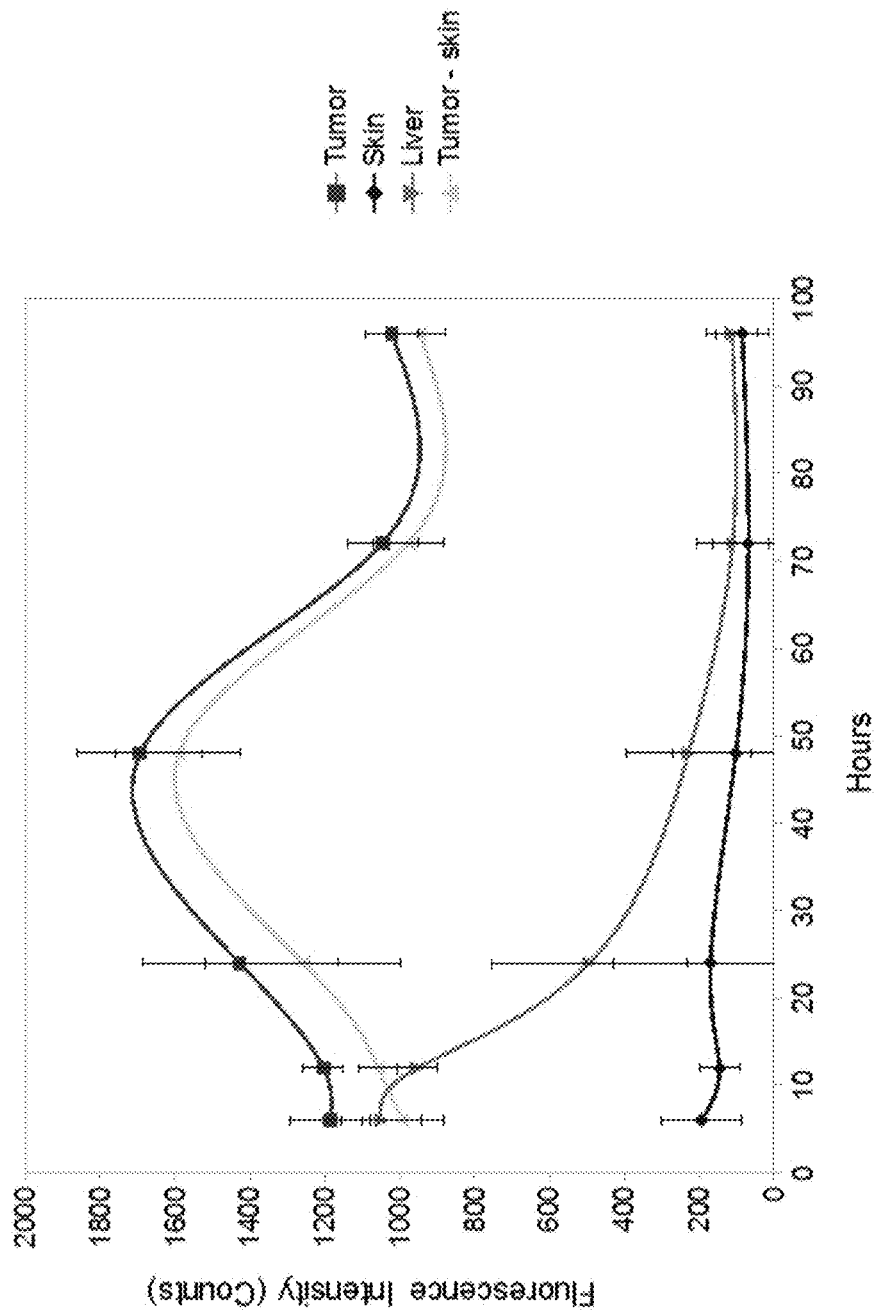

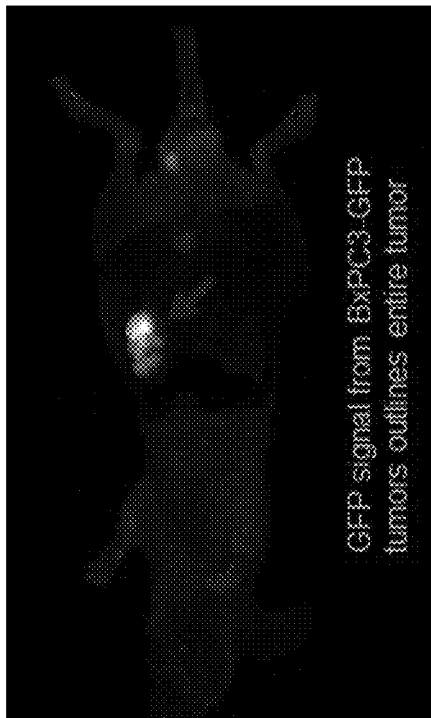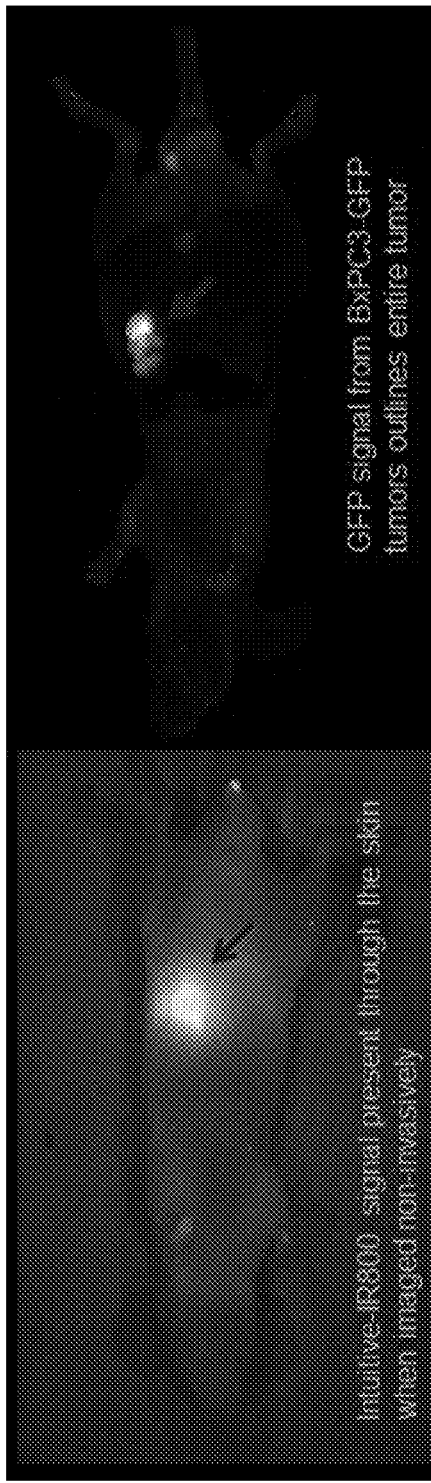

NIR-CONJUGATED TUMOR-SPECIFIC ANTIBODIES AND USES THEREOF

PRIORITY CLAIM

This application is a continuation of U.S. application Ser. No. 16/993,950, entitled "NIR-CONJUGATED TUMOR-SPECIFIC ANTIBODIES AND USES THEREOF," filed Aug. 14, 2020, which is a continuation of U.S. application Ser. No. 15/880,454, entitled "NIR-CONJUGATED TUMOR-SPECIFIC ANTIBODIES AND USES THEREOF," filed Jan. 25, 2018, and issued as U.S. Pat. No. 10,758,632 on Sep. 1, 2020, which claims priority to U.S. Provisional Application No. 62/455,401, entitled "NIR-CONJUGATED HUMANIZED ANTI-CEA ANTIBODY AND USES THEREOF," filed Feb. 6, 2017, which is incorporated herein by reference in their entirety, as if fully set forth herein.

GOVERNMENT INTEREST

This invention was made partially with government support under Grant No. CA142669, awarded by National Institutes of Health (NIH). The Government has certain rights in the invention.

FIELD OF THE INVENTION

The present invention relates to the fields of immunology, antibodies and conjugates, molecular biology, cancer diagnosis, and cancer therapy. In particular, this invention provides fluorophore-conjugated humanized tumor-specific antibodies such as anti-carcinoembryonic antigen (CEA) antibodies and/or anti-tumor-associated glycoprotein 72 (TAG-72) antibodies for detection and surgical resection of CEA positive diseases. The disclosed fluorophore-antibody conjugates demonstrate improved contrast for fluorescence guided oncologic surgeries.

BACKGROUND

There is an unmet clinical need in the care of patients with certain types of cancer for better preoperative and intraoperative tumor imaging techniques. There remains a high rate of both local and distant recurrence after surgical resection. Furthermore, accurate preoperative staging of tumor remains a challenge for clinicians. Improved techniques of delineating accurate tumor margins at the time of surgery and also identifying small volume metastatic disease would be of great help for improving outcomes for patients with cancer. The disclosed technology can be applied to cancer diagnosis, cancer prognosis, cancer treatment, tumor imaging, and imaging assisted surgery.

SUMMARY OF THE INVENTION

In one aspect, disclosed herein is an antibody conjugated with a detectable label for detecting CEA-positive diseases and/or the presence and location of tumor. In some embodiments, the detectable label is a fluorophore or a radioactive label. The antibody is conjugated to a fluorophore, labeled with a radioactive isotope, or both. The antibody conjugate can be used for tumor imaging before or during a surgery to direct surgical resection of tumors in a subject suffering from cancers, for example, CEA-expressing cancers or TAG-72-expressing cancers such as colorectal cancer, pancreatic cancer (e.g., pancreatic adenocarcinoma), gastric cancer, lung cancer, breast cancer, ovarian cancer, and medullary thyroid cancer. The antibody conjugate disclosed herein includes an anti-CEA antibody or anti-TAG-72 antibody conjugated to a near-infrared (NIR) fluorophore. In some embodiments, the anti-CEA antibody or the anti-TAG-72 antibody is a humanized antibody. In some embodiments, the anti-CEA antibody or the anti-TAG-72 antibody is a monoclonal antibody. In some embodiments, the antibody is humanized anti-CEA T84.66-M5A antibody. In some embodiments, the anti-TAG-72 antibody is humanized anti-TAG-72 CC49 antibody. In some embodiments, the NIR fluorophore is Li-Cor IRDye®800CW-NHS (IRDye®800) or Intuitive IR800 free acid (Intuitive IR800).

In another aspect, disclosed herein is a method of detecting or localizing in a subject a tumor that expresses CEA or TAG-72 by administering the antibody-fluorophore conjugate disclosed herein to the subject and scanning the subject with a scanning device at various time points after administration. The time points of scanning depend on the antibody-fluorophore conjugate tumor targeting, pharmacokinetics and blood clearance properties. For example, the subject is scanned within 6 hours, within 8 hours, within 10 hours, within 12 hours, within 24 hours, within 36 hours, within 48 hours, within 72 hours, within 96 hours, or within 120 hours of administration of the conjugate. In some embodiments, the subject is scanned on the same day of surgical resection. In some embodiments, the conjugate is administered to the subject by intravenous injection. In some embodiments, the subject suffers from a CEA-positive cancer or a TAG-72-positive cancer such as colorectal cancer, pancreatic cancer (e.g., pancreatic adenocarcinoma), gastric cancer, lung cancer, breast cancer, ovarian cancer, and thyroid cancer. In some embodiments, the subject suffers from colorectal cancer, pancreatic cancer, or ovarian cancer. In some embodiments, the methods disclosed herein employ an antibody which is labeled with a fluorophore, a radioactive label, or both.

In another aspect, disclosed herein is a method of tumor imaging to direct surgical resection of a CEA-expressing tumor or a TAG-72-expressing tumor by administering the antibody-fluorophore conjugate disclosed herein to the subject and scanning the subject with a scanning device at various time points after administration and before or during surgery to guide resection of the tumor. For example, the subject is scanned within 6 hours, within 8 hours, within 10 hours, within 12 hours, within 24 hours, within 36 hours, within 48 hours, within 72 hours, within 96 hours, or within 120 hours of administration of the conjugate. In some embodiments, the conjugate is administered to the subject by intravenous injection. In some embodiments, the subject suffers from a CEA-positive cancer or a TAG-72-positive cancer such as colorectal cancer, pancreatic cancer (e.g., pancreatic adenocarcinoma), gastric cancer, lung cancer, breast cancer, ovarian cancer, and thyroid cancer. In some embodiments, the subject suffers from colorectal cancer, pancreatic cancer, or ovarian cancer. In some embodiments, the methods disclosed herein employ an antibody which is labeled with a fluorophore, a radioactive label, or both.

BRIEF DESCRIPTION OF THE DRAWINGS

The patent application file contains at least one drawing executed in color. Copies of this patent or patent application publication with color drawing(s) will be provided by the Office upon request and payment of the necessary fee.

FIG. 5A shows that the fluorescent antibody bound the CEA-expressing BxPC-3-GFP human pancreatic cancer cell line by a staining with M5A-IRDye®800. Merged images of the GFP and M5A-IRDye®800 channels show the fluorescent-antibody localized at cell surfaces. FIG. 5B shows that no fluorescent antibody binding to the CEA-negative MiaPACA-2 human pancreatic cancer cell line expressing RFP by a staining with M5A-IRDye®800. Merged images of the RFP and M5A-LICOR800 channel show absence of antibody cell localization.

FIG. 7 shows a close-up view of the non-invasive imaging of satellite lesions by M5A-IRDye®800 in a patient derived orthotopic xenograft model (PDOX) for pancreatic cancer.

FIG. 8A shows M5A-IRDye®800 time course of fluorescence intensity. Fluorescence intensity of M5A-IRDye®800 at 6, 12, 24, 48, 72, and 96 hours after injection. Tumor (red line, square markers), skin (blue line, diamond markers), liver (green line, downward arrowhead markers), and tumor signal adjusted for skin background noise (yellow line, upward arrowhead markers) are represented.

FIGS. 13A-13D show the images in surgical orthotopic implant of BxPC3-GFP cells using 75 µg dye, imaged at 72 hours after injection of the dye. FIG. 13A shows that Intuitive-IR800 signal presented through the skin when imaged non-invasively. FIG. 13B shows the white light post-laparotomy view showing the location of the tumor. FIG. 13C shows that the GFP signal from BxPC3-GFP tumors outlined the entire tumor. FIG. 13D shows that 800 nm signal from Intuitive-IR800 dye also outlined the entire tumor area.

DETAILED DESCRIPTION

Fluorescence Guided Surgery (FGS)

Figure 1:
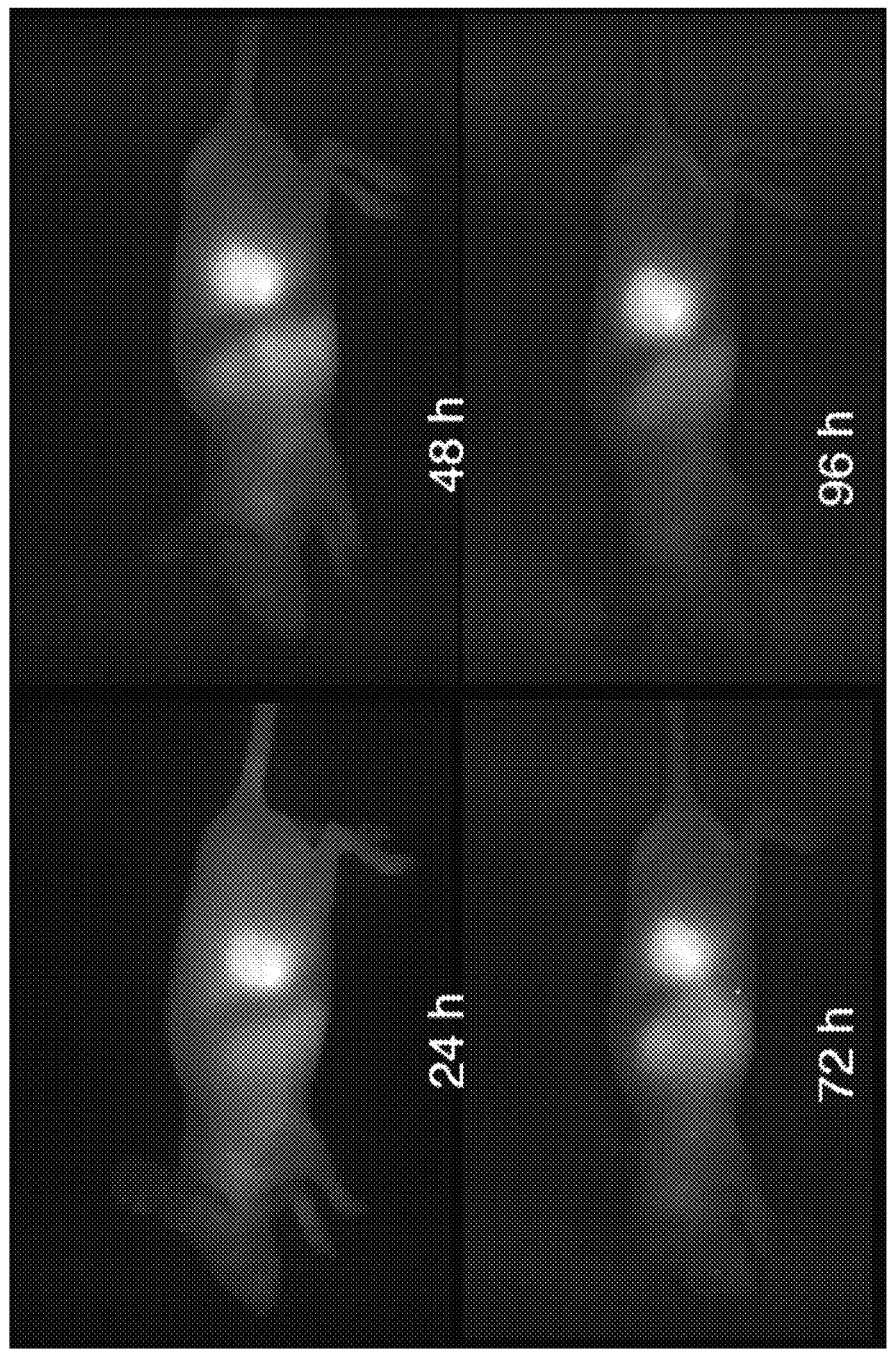
FIG. 1 shows non-invasive NIR imaging of M5A antibody conjugated to IRDye®800 in a mouse model bearing colorectal cancer HT29 xenograft tumor at 24 hours, 48 hours, 72 hours, and 96 hours post-injection of the conjugate.

Fluorescence guided surgery (FGS) combines advanced imaging platforms with targeted fluorescent agents to enhance neoplasms and improve their intraoperative detection by the surgeon (1). One technique is to covalently bind organic dye to a monoclonal antibody of a known tumor-specific antigen (2). One such tumor biomarker that is being developed preclinically is anti-carcinoembryonic antigen (CEA) antibodies to target and label human colorectal cancer in nude mouse models (3-6). Mouse and chimeric (mouse/human) antibodies against CEA have been strongly labeled with fluorescent dye and are capable of enhancing visualization of submillimeter tumor deposits (5) and successful FGS (7, 8). IRDye®800 can be broadly used in clinical setting with IR800 optical detection units. This technique has been applied to human clinical trials to localize squamous cell carcinoma of the head and neck using a cetuximab-IRDye®800 conjugate (9, 21).

The success of a curative surgery for cancer is dependent on the complete removal of all cancer cells. Increasing the surgeon's ability to detect cancer before and during the operation has the dual benefit of identification of disease that can be fully resected and recognizing locally advanced disease that cannot. FGS has the potential to advance the ability to recognize where an individual's disease actually is rather than relying on an understanding of where it most likely should be. With applications in staging laparoscopy, tumor localization, real-time assessment of margins during FGS, and surveillance for local recurrence, fluorescence tumor labeling is an essential tool for improving outcomes in surgical oncology. Tumor visualization by the surgeon can be enhanced through fluorescent-antibody targeting.

Antibodies and Conjugates Thereof

Previous studies with a fluorescent anti-CEA antibody have shown great promise for fluorescent image guided surgery of pancreatic cancer in mice (6, 7, 15-18). However, these studies were performed using a mouse or chimeric anti-CEA antibody and will need a humanized version to translate to the clinic. A humanized anti-CEA antibody (M5A mAb) has been in a Phase I radioimmunotherapy clinical trial and is currently in a pilot Cu-64 Positron Emission Tomography (PET) imaging trial (10, 19, 20). The humanized anti-CEA M5A antibody is currently undergoing clinical trials for PET imaging conjugated with Cu-64 and for radiotherapy conjugated with Y-90 (NCT02293954, NCT00645060). As disclosed herein, it is a highly specific probe for fluorescence in-situ tumor labeling.

In an effort to improve therapeutic efficacy and increase clinical relevance, Yazaki et al. replaced the murine section of the chimeric anti-CEA antibody with structurally similar "human" fragments through a technique known as complementary determining region (CDR) grafting (10). This "humanized" antibody was selected for the current study to determine the extent of labeling of CEA positive cancers, such as human colorectal cancer and pancreatic cancer, in an orthotopic mouse model.

Thus, the anti-CEA humanized M5A is a versatile antibody for use in targeting a number of CEA-positive malignancies. In addition to showing promise as a probe for in-situ tumor-specific fluorescence delivery, it is being evaluated as a radioactive diagnostic imaging modality and as a therapeutic treatment.

Anti-CEA antibodies and humanized anti-CEA antibodies are disclosed in, e.g., U.S. Pat. Nos. 7,776,330 and 7,273,608, the entire contents of which are incorporated herein by reference. These antibodies exhibit high levels of binding affinity and specificity for CEA. Moreover, the humanized antibody has exhibited the ability to specifically target tumors that express CEA in vivo, making it a potentially powerful tool for the detection and treatment of such tumors. In some embodiments, the humanized anti-CEA T84.66-M5A antibody disclosed in the above-mentioned US Patents can be used. It is within the purview of one skilled in the art to make necessary modification of this antibody, for example, to facilitate the antibody conjugating to a suitable fluorophore without significantly lowering the binding affinity and specificity for CEA and without significantly decreasing the ability to specifically target CEA-expressing tumors in vivo. In some embodiments, modified humanized anti-CEA antibodies or fragments thereof can be used as long as the binding affinity and specificity for CEA in vivo are not significantly compromised.

The methods and technology disclosed herein can be carried out by using any tumor-specific antibody which is conjugated to a fluorophore, labeled with a radioactive isotope, or both. Depending on the specific type tumor or the specific biomarker for the tumor, one can choose a suitable antibody for detection and localization of the tumor. Such antibodies include but are not limited to anti-CEA antibodies and anti-TAG-72 antibodies. It is within the purview of one of ordinary skill in the art to use humanized antibodies or monoclonal antibodies to maximize the specific binding and tumor detection thereby optimizing the tumor imaging effects. For example, the anti-TAG-72 antibody is humanized anti-TAG-72 CC49 antibody.

As used herein, the term "antibody" refers to monoclonal antibodies, polyclonal antibodies, and antibody fragments prepared by recombinant nucleic acid techniques. The term may refer to an intact tetrameric immunoglobulin containing two complete light chains and two complete heavy chains, each with a variable region and a constant region. Alternatively, it may refer to a fragment thereof, such as an Fv fragment (containing only the variable regions of the light and heavy chains), an Fab fragment (containing the variable regions and some elements of the constant regions), a diabody, a single-chain antibody, or any other antibody fragment.

The term "humanized antibody" as used herein refers to an antibody containing structural elements of a human antibody (the acceptor) and the antigen binding site of a non-human antibody (the donor). "Humanized antibodies" contain a minimal number of residues from the non-human antibody. For instance, they may contain only the CDR regions of the non-human antibody, or only those residues that make up the hypervariable regions of the non-human antibody. They may also contain certain residues from outside the variable regions of the non-human polypeptide, such as residues that are necessary to mimic the structure of the non-human antibody or to minimize steric interference. In addition, humanized antibodies may contain residues that do not correspond to either the human or the non-human antibodies.

Fluorophore Dyes

IRD800 dyes, such as intuitive IR800 free acid and Li-Cor IRDye® 800 CW-NHS can be used as the fluorophore for this study. These dyes have a similar excitation and emission profile to indocyanine green (ICG), for which numerous clinically-available fluorescence imaging protocols are used (11, 12).

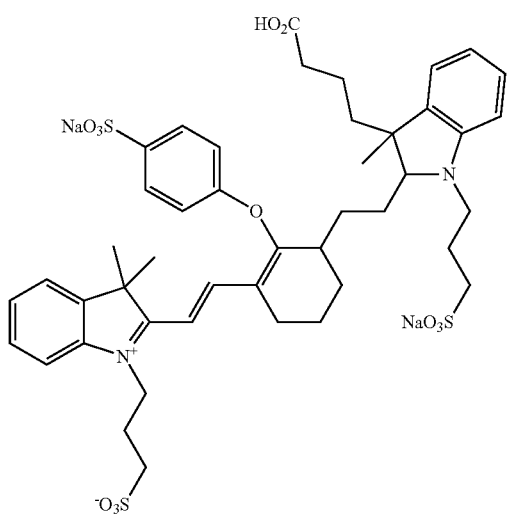

Intuitive IR800 free acid

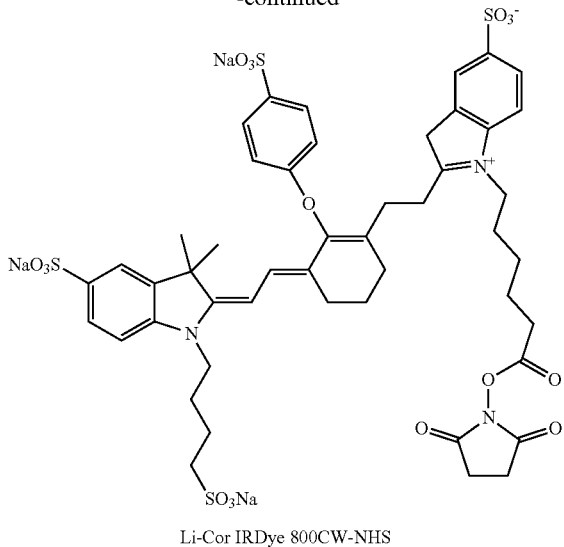

Li-Cor IRDye 800CW-NHS

Various anti-CEA antibody-fluorophore conjugates may have different circulation/clearance time. For example, the anti-CEA-Li-Cor IRDye®800 conjugate disclosed herein can be rapidly cleared from circulation due to the pharmacokinetics of the conjugate. The IRDye®800 is a hydrophobic molecule that is fully cleared from the blood stream by approximately 24 hours, significantly more rapidly than the monoclonal antibody alone which is cleared by approximately 72 hours (14). This results in greater accumulation in the liver and the kidneys and allows for fewer passages through the tumor circulation and thus less tumor enhancement. As demonstrated in the working examples, the anti-CEA-Intuitive IR800 conjugate had a much longer clearance time than the anti-CEA-Li-Cor IRDye®800 conjugate.

Conjugation Chemistry

Tumor enhancement with less hepatorenal involvement can be achieved through conjugation of the antibody/fluorophore in such a way that protects the hydrophobic region of the molecule, or by selecting a different fluorophore without such a region. For example, conjugating into the antibody IgG hinge has the potential to hide some of the hydrophobicity, the addition of sulfo chemical groups can add to the hydrophillicity, and the use of poly ethylene glycol derivative may shield the hydrophobicity.

Figure 2:
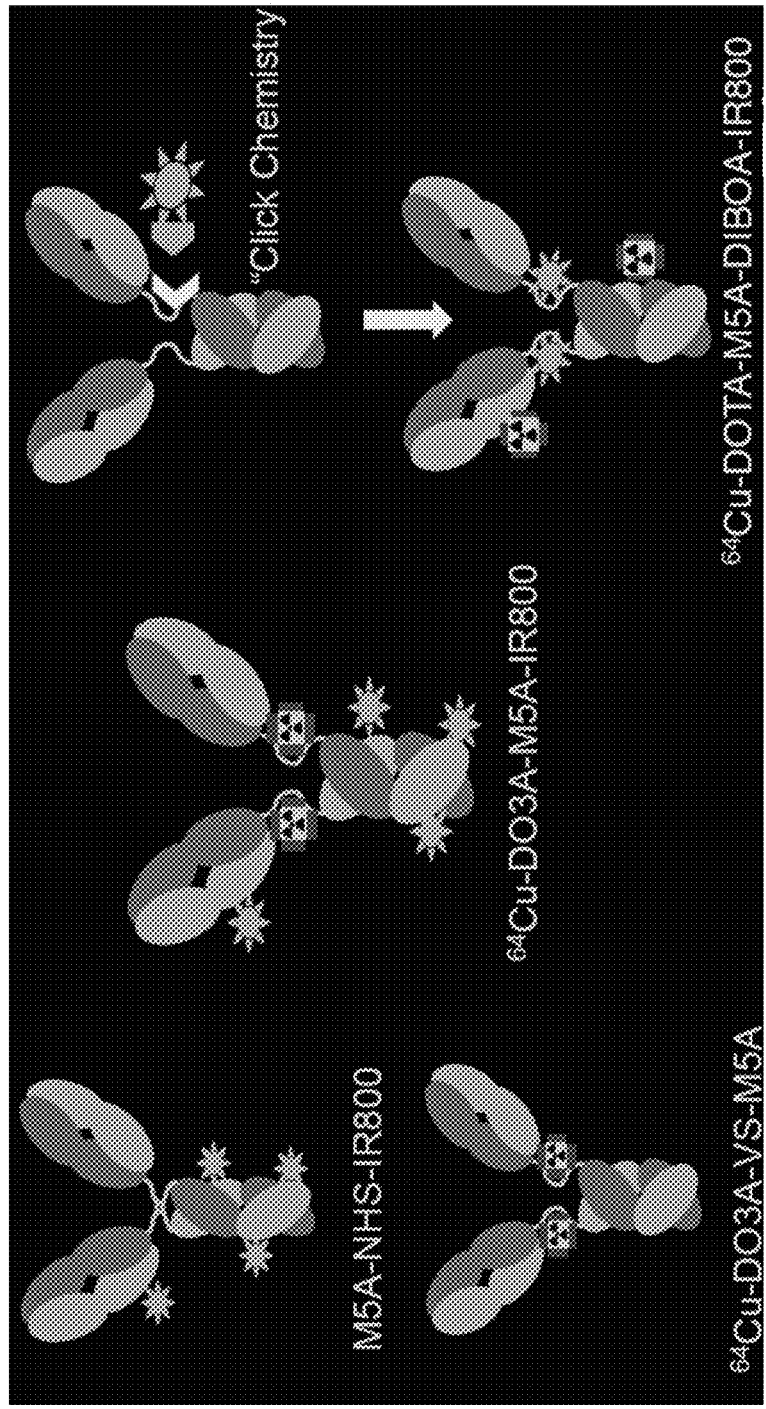
FIG. 2 demonstrates various conjugation schemes of a fluorescent label and/or a radioactive label to an antibody.

In some embodiments, the antibody can be conjugated to a fluorophore, as disclosed above. In some embodiments, the antibody can be conjugated to a radioactive label such as $^{64}Cu$, $^{125}I$, $^{131}I$, etc. via a chelating agent, such as 1,4,7,10-tetraazacyclododecane-1,4,7,10-tetraacetic acid (DOTA). In some embodiments, the antibody can be conjugated to both a fluorophore and a radioactive label to allow dual imaging. Various labeling techniques are illustrated in FIG. 2. For example, the antibody conjugated to a fluorophore and a radioactive label allows a general localization of the tumor site based on detection of the radioactive label, while the fluorescent signal guides tumor excision during the surgery.

Various antibody conjugation techniques known in the art can be used, such as covalent or non-covalent linkage, and click chemistry. Based on the specific label and antibody, one can select suitable conjugation technique and optimize the number of dye molecules conjugated to each antibody molecule for a desirable detection/imaging effect and blood clearance profile. The antibody can be conjugated to one or more molecules of a fluorophore, labeled with one or more molecules of a radioactive isotope, or both. In some embodiments, each antibody is conjugated to 1, 2, 3, 4, 5, 6, 7, or 8 molecules of fluorophore. In some embodiments, each antibody is conjugated to 3 molecules of the fluorophore.

Detection and Treatment of Colon Cancer

HT-29 was selected as the cell line for our study because it is known to express CEA and it reliably grows in orthotopic colon cancer models in nude mice when tumor fragments are sutured to the mesenteric border of the mouse cecum (6). It has been previously demonstrated that serosal transplantation of intact colon tumor tissue in nude mice (surgical orthotopic implantation) allows a clinical pattern of metastases to occur (24,25) which seems to be a general phenomenon for other tumor types (26-28).

It has been previously shown that NIR dye can penetrate through a layer of skin and body wall in a murine model which suggests that intraluminal tumors would still be clearly visible when imaged through the colonic wall (29). An orthotopic mouse model with HT-29 human colorectal tumors growing on the mucosa of the descending colon was developed to better resemble the clinical disease (30). Fluorescence was observed along the entire descending colon after intracolonical administration of lectin-immobilized fluorescent nanospheres from the anus (30). As disclosed herein, tumors grew to be 4-7 mm in diameter at the time of imaging. Submillimeter tumor deposits during FGS and even single cancer cells could be identified with proper magnification, which could lead to more rapid identification of lymph node metastasis with greater accuracy (31).

It was previously shown in an orthotopic model of colon cancer that FGS improves outcome in colon cancer compared with bright light surgery by increasing the percentage of R0 resections, decreasing recurrence, and increasing survival (5,8). The technology disclosed herein demonstrates that further increases in the benefits of FGS for colon cancer can be made because of increases in tumor visibility afforded by the NIR-conjugated humanized antibody.

Various mouse models can be used such as a nude mouse model that lacks an immune system and a humanized NOD Scid Gamma (NSG) mice implanted with patient-derived orthotopic xenografts colon cancers. NSG mice are engrafted with human immune cells. This will allow evaluation of patient tumors in an immunocompetent model.

The working examples demonstrate that the fluorophore conjugated humanized antibodies disclosed herein can rapidly and effectively label CEA-expressing human colon cancer in an orthotopic nude mouse model. Given the ability of this technology to target and label tumors with great specificity, the conjugates have clinical uses in fluorescence-guided surgery.

Detection and Treatment of Pancreatic Cancer

Pancreatic cancer is an aggressive malignancy with a poor survival rate. The only curative treatment for pancreatic cancer is surgical resection with true negative margins. However delineation of tumor margins is challenging in practice. Surgeons commonly use visual and tactile feedback along with clinical judgment based on pre-operative cross sectional imaging to determine the boundaries of resection. This is insufficient; as many as 80% of pancreatic resections are considered R1 (greater than 1 mm clearance) and this remains an independent determinant of post-operative outcome (22,23). Fluorescence image guidance is an approach that can be utilized within the operative field to enhance contrast and visualization of the neoplasm.

The BxPC-3 tumor was selected as a high CEA expressing human pancreatic cancer cell line as previously shown by flow cytometry (15, 32). Cellular microscopy confirmed binding of the fluorescent antibody to this cell line in-vitro and its sub-cellular localization at the surface membrane, which is consistent with its known status as a cell surface glycoprotein. M5A-IRDye®800 is a probe that binds specifically to CEA as it did not demonstrate any binding at the same concentration in a CEA-negative MiaPaca-3 pancreatic cancer cell line.

In-vivo studies highlight the improvements in visualization using a near-infrared wavelength. GFP is a fluorescent protein in the visible wavelength that is subject to hemoglobin quenching. The fluorescence signal is limited with increasing tissue depth. The use of near-infrared fluorophores improves tissue penetration with decreased background noise (33). LICOR-IRDye®800CW (IRDye®800) is a promising dye for future clinical use as it is a biocompatible fluorophore in the near-infrared spectrum and it has been validated in several Phase I/II clinical trials for fluorescence-guided surgery (FGS) of head and neck cancer (NCT02415881, NCT01987375, NCT02736578) (9,34). Additionally, the emission and absorption spectra of LICOR-IRDye®800CW overlap with that of indocyanine green (ICG). A number of FDA-approved imaging platforms exist for imaging ICG and the spectral overlap permits visualization of IRDye®800 labeled probes (35,36). However, further improvement of the fluorophore-antibody conjugates is needed for precise surgery excision of various tumors while lowering the background caused by the conjugate circulation and accumulation in the body of the patient.

As demonstrated in the working examples, time course studies showed a tumor-specific signal present as early as 6 hours. However there was non-specific background noise present over the liver, bladder and the skin that decreased over time as the tumor signal increased. Despite the background noise, there was an adequate tumor to background signal at all time points evaluated. A nonspecific background signal over the skin and soft tissue is likely attributable to the circulating probe not yet bound to the tumor or eliminated. This skin and soft tissue signal is minor and will not pose an issue for this construct in clinical surgical use. The signal over the bladder is likely due to a degree of proteolytic degradation and renal elimination of resulting peptides and fluorophore. As most patients undergoing major oncologic surgery are catheterized, this will not likely be an issue in the operative field. However there is significant accumulation of the antibody-dye conjugate at the liver beyond expected for known antibody hepatic accumulation (37,38). This liver signal may be due to additional hydrophobicity from LICOR-IRDye®800CW. This signal could potentially be an issue, as it can potentially mask CEA-positive hepatic malignancies or CEA positive colorectal liver metastases. Despite the initial fluorescence at the liver, the signal rapidly decreases after 12 hours and returns close to baseline near 48 hours and beyond. The addition of polyethylene glycol (PEG) groups or attachments of the fluorophore in a conformation that may mask the hydrophobic moieties, could be approaches to improve this issue (39). An example of a PEG-modified IR800 dye (Br-IR800-PEG Sidewinder) is shown as follows:

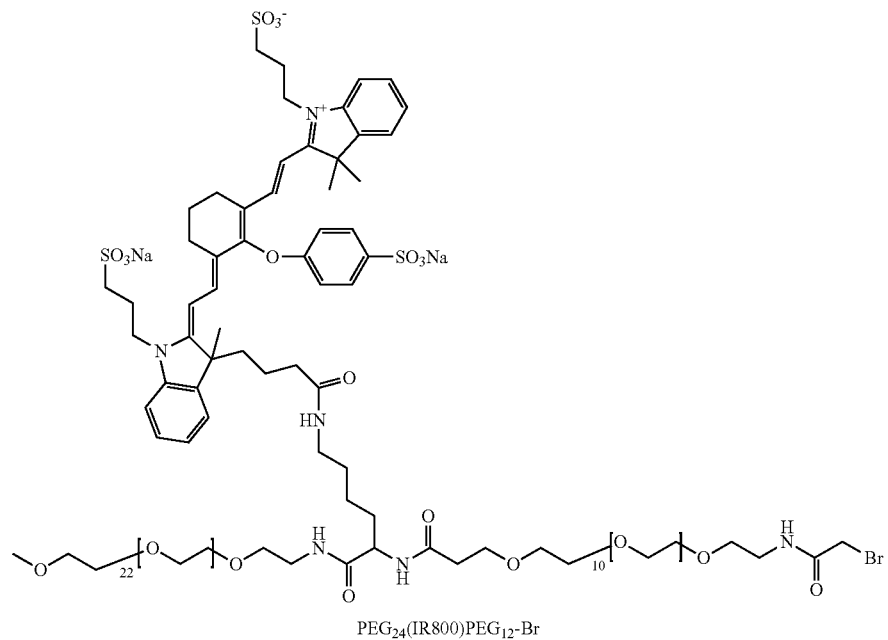

PEG$_{24}$(IR800)PEG$_{12}$-Br

As demonstrated in the working examples, humanized anti-CEA-800 tumor-specific dye specifically labeled orthotopically implanted pancreatic cancer xenografts. The dye successfully co-localized with GFP tagged tumor cells. The longer wavelength allowed for deeper tissue penetration, particularly in areas of the tumor covered by normal pancreatic parenchyma.

Administration of the Antibody Conjugates

The humanized tumor-specific antibody such as an anti-CEA or anti-TAG-72 antibody can be conjugated to a variety of labels, particularly fluorescent labels and/or radioactive labels, and administered to a subject for detection or localization of a tumor expressing CEA or TAG-72 by subcutaneous, peritoneal, intravenous, intravascular, intramuscular, intradermal or transdermal injection, among other methods. These labels may be linked to the humanized antibodies by covalent binding, affinity binding, intercalation, coordinate binding, or complexation, among other methods.

For detection and localization of tumors expressing CEA or TAG-72, the humanized antibody conjugate disclosed herein may be administered at a dose sufficient for detection by a scanning device. This dosage will be dependent on the type of label being used. The type of scanning device to be used will vary depending on the label being used, and one skilled in the art will easily be able to determine the appropriate device. For detection of a tumor expressing CEA or TAG-72, the humanized antibody conjugate disclosed herein may be prepared as a formulation within pharmaceutically acceptable media. This formulation may include physiologically tolerable liquids, gels, solid carriers, diluents, adjuvants, or excipients, or some combination thereof.

As demonstrated in the working examples, various humanized fluorophore-conjugated and/or radioactive-labeled antibodies can be used in tumor labeling for successful treatment of various cancers, such as colorectal cancer, pancreatic cancer, and ovarian cancer. The working examples also demonstrate the feasibility, kinetics, and advantages of using humanized anti-CEA antibodies conjugated to different near-infrared IR800 fluorophores or radioactive isotopes such as $^{64}Cu$, for in-situ tumor specific labeling of orthotopic colon cancer or pancreatic cancer xenografts.

The technology disclosed herein increases the surgeon's ability to detect and localize cancer during the operation, and therefore it has the dual benefit of identification of disease that can be fully resected and recognizing locally advanced disease that cannot. FGS allows precise localization of an individual's disease rather than relying on an understanding of where it most likely should be. With applications in staging laparoscopy, tumor localization, real-time assessment of margins during FGS, and surveillance for local recurrence, fluorescence tumor labeling is an essential tool for improving outcomes in surgical oncology.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1: Materials and Methods for Experiments in a Colon Cancer Model

Cell Culture: The human colon cancer cell line HT-29 was selected and was maintained in Roswell Park Memorial Institute (RPMI) medium (Gibco-BRL, Grand Island, NY) supplemented with 10% fetal calf serum (FCS; Hyclone, Logan, UT) and 1% penicillin/streptomycin (Gibco-BRL). The cells were cultured at 37° C. in a 5% $CO_2$ incubator.

Conjugation of Antibody to Fluorophore: Humanized monoclonal antibody hT84.66-M5A specific for CEA was labeled with IRDye®800 in PBS (lot: 03FEB2016NB1, Duarte, CA). The humanized antibody for CEA was covalently bound to the IRDye®800 NIR dye through an ester reaction. Briefly, the antibody was combined with reconstituted reactive dye at a starting molar ratio of 10:1 (dye: antibody) in 0.1 M sodium bicarbonate and allowed to incubate at room temperature for 1 hour then overnight at 4° C. Excess dye was removed through centrifuge purification columns, e.g., an Amicon stirred cell concentrator (Millipore, Billerica, MA). The final concentration of antibody-dye conjugate was 6.6 mg/ml with an average of 1.6 dye molecules per IgG. The antibody-dye conjugate was stored in the 4° C. refrigerator and was protected from light.

Animal Care: Athymic nu/nu nude mice (AntiCancer, Inc., San Diego, California), between 4 and 6 weeks of age were maintained in a barrier facility at AntiCancer, Inc., on high-efficiency particulate air-filtered racks. The animals were fed with autoclaved laboratory rodent diet (Teckland LM-485; Western Research Products, Orange, California). All surgical procedures and imaging were performed with the animals anesthetized by intramuscular injection of 0.02 mL of a solution of 50% ketamine, 38% xylazine, and 12% acepromazine maleate. All animal studies were conducted in accordance with the principles and procedures outlined in the NIH Guide for the Care and Use of Animals under PHS license number A3873-1.

Subcutaneous Injection of Tumor Cells: The HT-29 line of human colorectal cancer cells were harvested after 2 weeks of growth by trypsinization and washed with serum-free medium. $1\times10^6$ cells were combined with 100 µl Matrigel (Corning, Tewksbury, MA) and subcutaneously injected into the bilateral flanks of 5 athymic female nu/nu mice at 6 weeks of age. The tumors were allowed to grow until they reached a diameter of approximately 10 mm, which occurred after 3 weeks.

Passage and Orthotopic Implantation of HT-29 Tumor: Orthotopic human colon cancer xenografts were established in nude mice by suturing a small fragment of HT-29 tumor on the mesenteric border of the mouse cecum. To start, a 10 mm subcutaneous HT-29 tumor was resected and cut into 2 $mm^3$ fragments. The fragments were then sutured to the cecum of 5 additional nude mice for orthotopic implantation using 8-0 nylon sutures. The tumors were allowed to grow for 4 weeks at which point three had successful orthotopic tumor growth and were selected for fluorescence imaging. The remaining two mice did not survive the 4-week recovery period. Small tumor fragments were also implanted in the bilateral flanks of each mouse to track the growth of the tumors.

Antibody-Dye Conjugate Delivery: Four weeks after the orthotopic implantation of HT-29 tumor the animals were given a single intravenous dose of 100 µl of conjugated anti-CEA (anti-CEA-IRDye®800CW) via tail vein injection. Each dose was 75 µg.

Mouse Imaging: Images were obtained with the Pearl Trilogy Small Animal Imaging System (Li-Cor, Lincoln, NE) pre-injection, 5 min post-, 5 hours post-, 24 hours post-(with laparotomy views), and 48 hours post-injection (with laparotomy views) with both 700 nm and 800 nm channels. Images were evaluated using Image Studio. Signal from the 700 nm channel was displayed red and signal from the 800 nm channel was displayed as green.

Example 2: Tumor Imaging with Humanized Anti-CEA-IRDye®800 Conjugate in a Colon Cancer Model This example demonstrates that humanized anti-CEA-IRDye®800 can rapidly and effectively label CEA-expressing human colon cancer in an orthotopic nude mouse model. Given the ability of the disclosed technology to target the label tumor with great specificity, anti-CEA-IRDye®800 can be used for fluorescence-guided surgery in clinical settings.

The purpose of this experiment was to label colon cancer by means of a clinically-relevant humanized anti-CEA antibody labeled with a near infrared 800 nm fluorophore. Selecting IRDye®800CW as the fluorophore allows the use of the indocyanine green (ICG)-based imaging instrument that is rapidly expanding in clinical use (13). Thus, successful labeling colon cancer with these two components serves as a bridge from the preclinical work with tumor labeling to practical surgical applications clinically for CEA-expressing cancers.

The current pilot studies using M5A (a humanized anti-CEA antibody) conjugated to a variety of fluorophores especially the near infrared IRDye®800 (Li-Cor Biosciences) showed promising results in the mouse model of colorectal cancer (see FIG. 1). As detailed below, laparotomy was performed 24 hours after labeling the tumors. When imaged through the 800 nm channel, the tumors were observed to be strongly labeled with anti-CEA-IRDye®800. At 48 hours laparotomy was repeated which again demonstrated strong labeling of the tumors through the 800 nm channel, but with a lower absolute intensity (in relative units), than at 24 hours for each of the three mice imaged.

Figure 3:
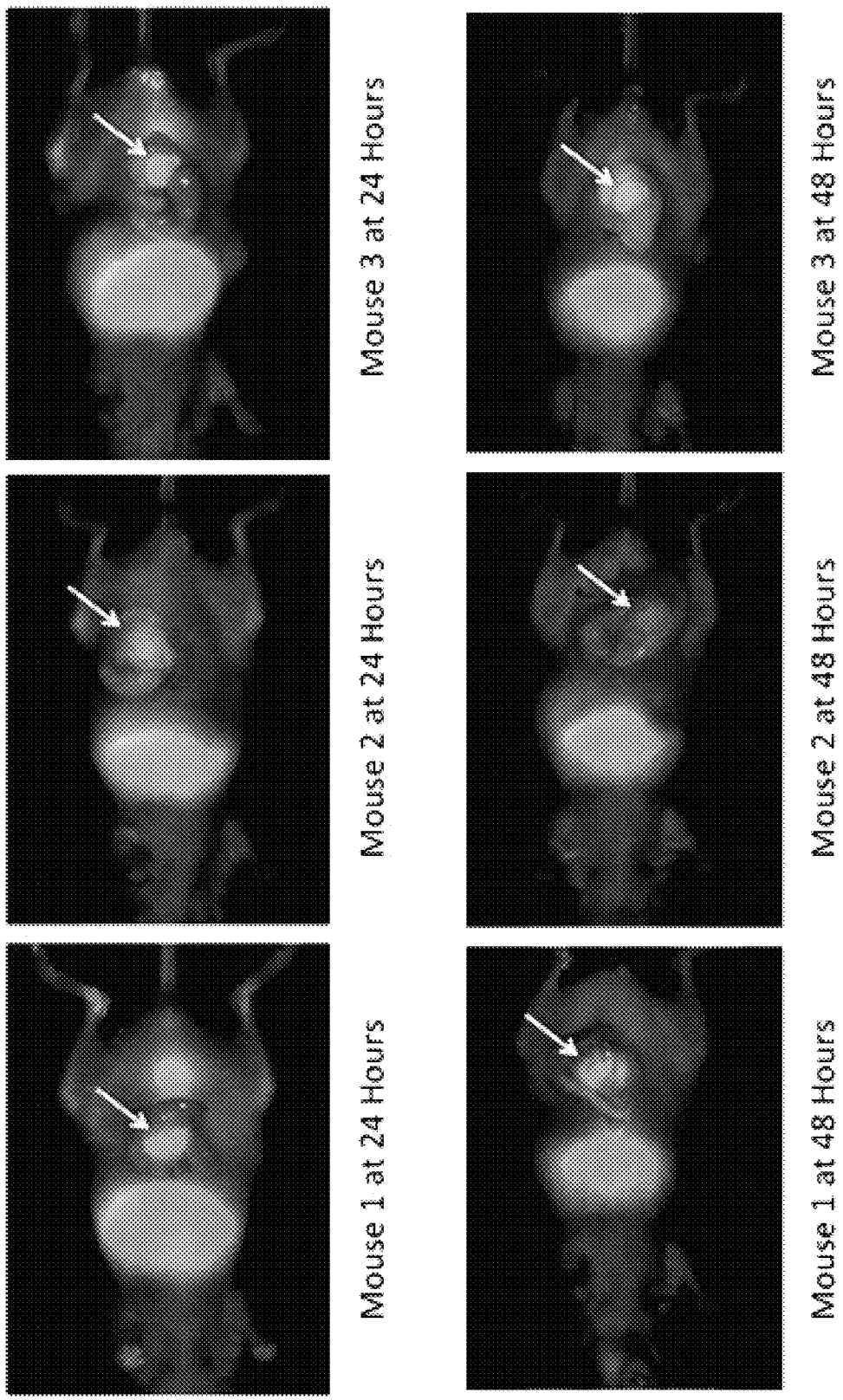
FIG. 3 shows that anesthetized mice were imaged using the Li-Cor Pearl Trilogy Small Animal Imaging System at 24 hours and 48 hours post-injection of the anti-CEA-IRDye®800 conjugate. In this series laparotomy was performed prior to acquiring images. The orthotopic colon cancer tumors were well enhanced with the targeted fluorophore (arrows). The images at 24 hours have stronger enhancement than at 48 hours. Red (700 nm) versus green (800 nm).

Three mice with orthotopic HT-29 colon cancers were treated with 75 µg of anti-CEA antibody-dye conjugates (anti-CEA-IRDye®800). Images were then acquired under anesthesia with the Pearl Trilogy Small Animal Imaging System (Li-Cor, Lincoln, NE) at 24 and 48 hours post injection. The tumors were imaged directly after performing a midline laparotomy and delivering the cecum and neoplasm through the incision. At this time the tumor was strongly enhanced using the 800 nm channel (green) in all three animals, as shown in FIG. 3. Normal gut was visualized through the 700 nm channel (red), due to the signal emitted from plant chlorophylls within the mouse chow. There was no appreciable difference in enhancement between the three animals. At 48 hours laparotomy was repeated which again demonstrated strong labeling of the tumors through the 800 nm channel, but with a lower absolute intensity (in relative units), than at 24 hours for each of the three mice imaged.

Figure 4:
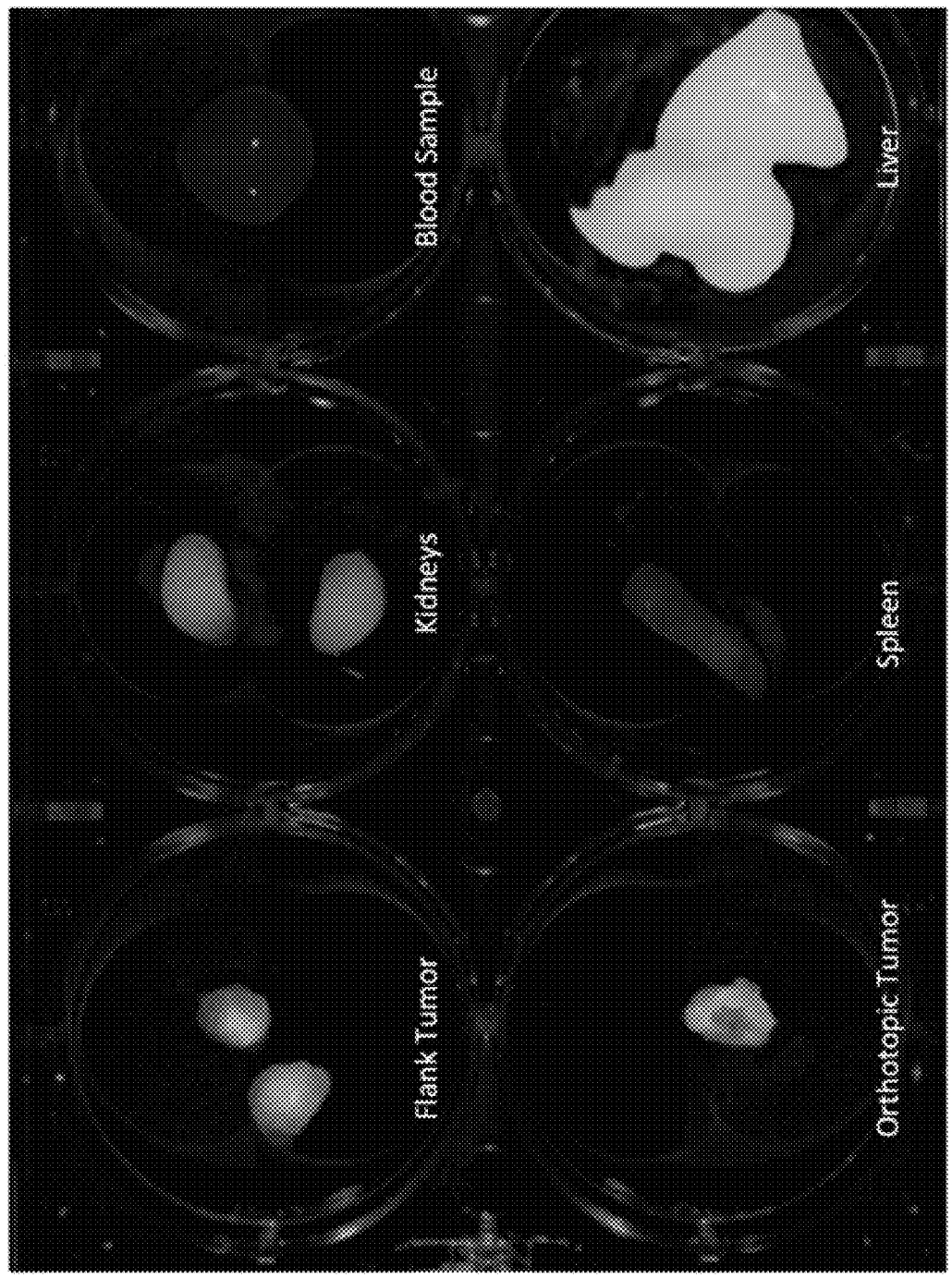
FIG. 4 shows that following sacrifice, images were taken of the flank tumors, orthotopic tumors, kidneys, spleen, blood sample, and liver to determine dye accumulation at 48 hours. Notably, the tumors are well enhanced and there is no dye remaining in the blood due to the rapid clearance of the dye from the circulation.

At 48 hours post injection, the mice were sacrificed via tail vein injection of 0.1 mL of a solution of 50% ketamine, 38% xylazine, and 12% acepromazine maleate and a necropsy was performed. Each mouse was carefully dissected to remove the bilateral flank tumors, the colon tumor, bilateral kidneys, spleen, blood sample, and the liver, each of which was carefully placed on a 6 well tissue culture plate, as shown in FIG. 4. Each organ or tumor was then imaged to determine the relative strength and accumulation of fluorescence signal at 48 hours. Both the flank and orthotopic tumors retained their fluorescence signal. Considerable uptake was also appreciated in the liver and kidneys because of metabolism of the antibody-dye conjugate. There was no fluorescence signal in the blood samples at 48 hours and minimal signal in the spleens.

Example 3: Materials and Methods for Experiments in a Colon Cancer Model

Tissue Culture: The human pancreatic cancer cell lines BxPC-3 (ATCC® CRL-1687™), stably expressing green fluorescent protein (GFP) and MiaPACA-2 (ATCC® CRL-1420™) expressing RFP, were maintained in Roswell Park Memorial Institute 1640 (RPMI-1640) medium (Gibco-BRL, Grand Island, NY). The medium was supplemented with 10% fetal calf serum (Hyclone, Logan, UT), 1% L-Glutamine, and 1% penicillin/streptomycin (Gibco-BRL). The cells were incubated at 37° C. in a 5% $CO_2$ incubator.

Antibody Conjugation: The humanized M5A mAb was developed by grafting the CDR region of the murine anti-CEA antibody mT84.66 onto the humanized anti-p185HER2 antibody (Trastuzumab) framework and expressed as previously described (10). The purified M5A antibody was conjugated with IRDye®800 (LI-COR Biosciences, Lincoln, NE) at a 10-fold molar excess of the esterified dye at room temperature for 1 hour. Concentrations of the M5A-IRDye®800 conjugate were determined by $Absorbance_{280}$. The final concentration of antibody-dye conjugate was 5.7 mg/mL with an average of 5-6 dye molecules per IgG based on mass spectrometry.

Immunofluorescence Imaging: BxPC-3-GFP and MiaPaca-2-RFP cells were grown overnight on cover slips coated with 0.1% gelatin ($5\times10^5$ cells per well). The cells were incubated with 200 nM of M5A-IRDye®800 for 1 hour at 37° C. After washing, the cells were fixed with 4% formaldehyde (Fisher Scientific, Waltham, MA) for 15 minutes and stained with 300 nM DAPI (Fisher Scientific, Waltham, MA) for 5 minutes. The cover slips were mounted on slides with ProLong Gold antifade reagent (Life Technologies, Grand Island, NY). Cells were imaged at 20× with a Nikon A1R Confocal laser microscope (Nikon Instruments, Melville, NY).

Animal Care: Immunocompromised nude nu/fox mice were maintained in a barrier facility on high-efficiency particulate air (HEPA)-filtered racks at AntiCancer Inc. Mice were maintained ad lib on an autoclaved laboratory rodent diet (Teckland LM-485; Western Research Products, Orange, CA, USA) and kept on a 12 hour light/12 hour dark cycle. All surgical procedures and intravital imaging were performed with the animals anesthetized by intramuscular injection of an anesthetic cocktail composed of ketamine 100 mg/kg (MWI Animal Health, Boise, ID), xylazine 10 mg/kg (VWR, Brisbane, CA), and acepromazine 3 mg/kg (Sigma, Saint Louis, MO). All animal studies were conducted in accordance with the principles and procedures outlined in the NIH Guide for the Care and Use of Animals under PHS Assurance Number A3873-1.

In-Vivo Studies: BxPC-3-GFP pancreatic cancer cells ($1\times10^6$ cells per animal) were injected subcutaneously into the flank of nude mice. The tumors were allowed to grow for 4 weeks or until 7-10 mm in size. The tumors were harvested and 2 $mm^3$ fragments were implanted into the pancreatic tail of recipient nude mice to create orthotopic models of pancreatic cancer. After the tumors developed for 2 weeks, 75 µg of M5A-IRDye®800 was injected via tail-vein. Three mice per time point were sacrificed and imaged at 6, 12, 24, 48, 72, and 96 hours after injection using the Maestro CRI imaging system (Perkin Elmer, Waltham, MA). The images were acquired at the GFP wavelength (Excitation 488 nm, emission 510 nm) and IRDye®800 wavelength (Excitation 778 nm, emission 800 nm). Fluorescence intensity was quantified at the skin and tumor after spectral unmixing using the Maestro CRI software. Fluorescence intensity was adjusted for background signal at the skin by subtracting the intensity value at an area of adjacent skin to the intensity value at the tumor. Tumor-to-background ratio (TBR) was calculated by dividing the intensity value at an area of adjacent skin to the intensity value at the tumor.

Example 4: Tumor Imaging with Humanized Anti-CEA-IRDye®800 Conjugate in a Pancreatic Cancer Model This example demonstrates that humanized anti-CEA-IRDye®800 can successfully target human pancreatic cancer in-situ using orthotopic xenograft mouse models, with useful kinetics and a favorable tumor-to-background ratio.

Figure 5A:
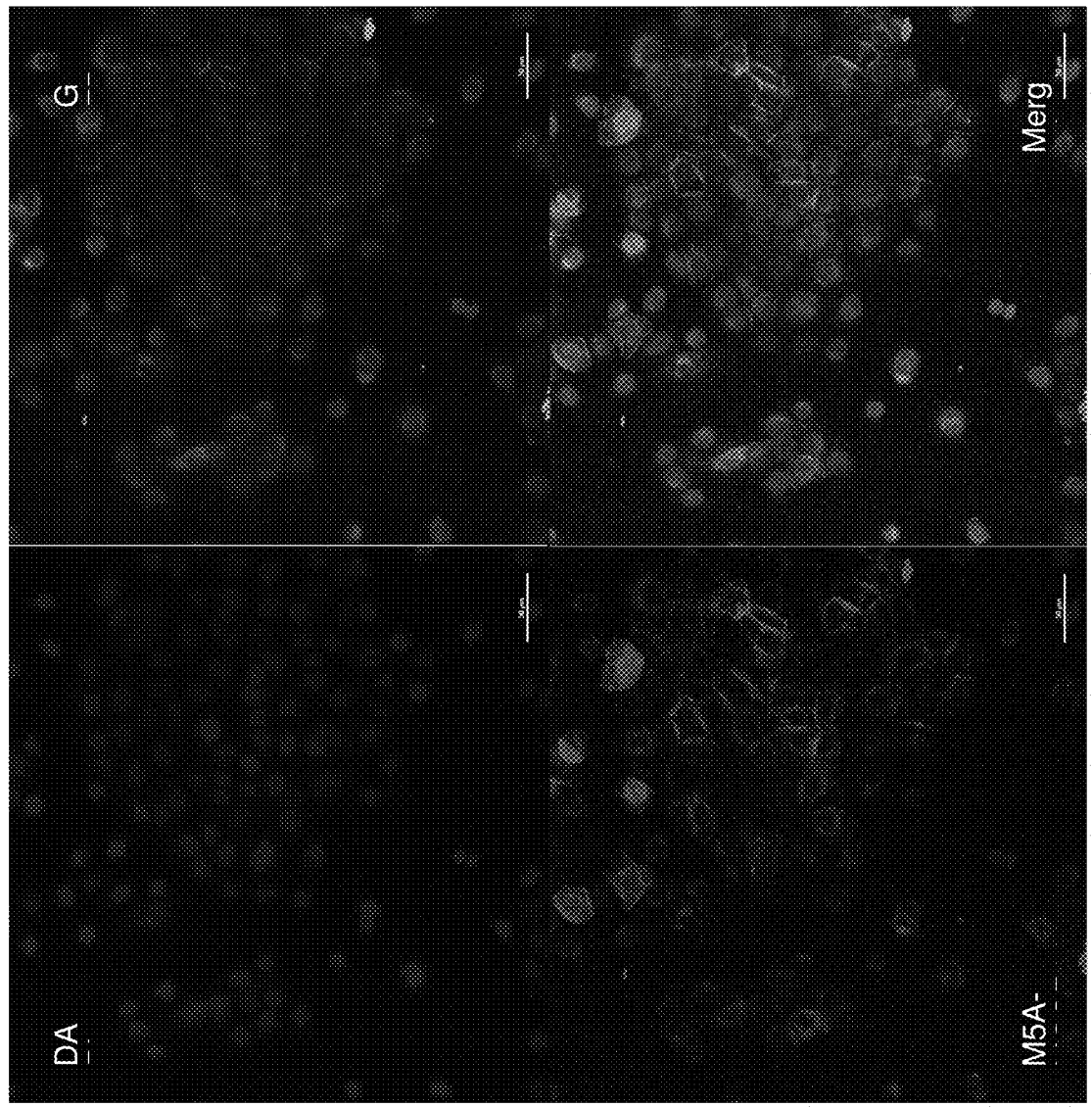
FIGS. 5A and 5B show M5A-IRDye®800 binding to BxPC3-GFP human pancreatic cancer cell line.
Figure 5B:
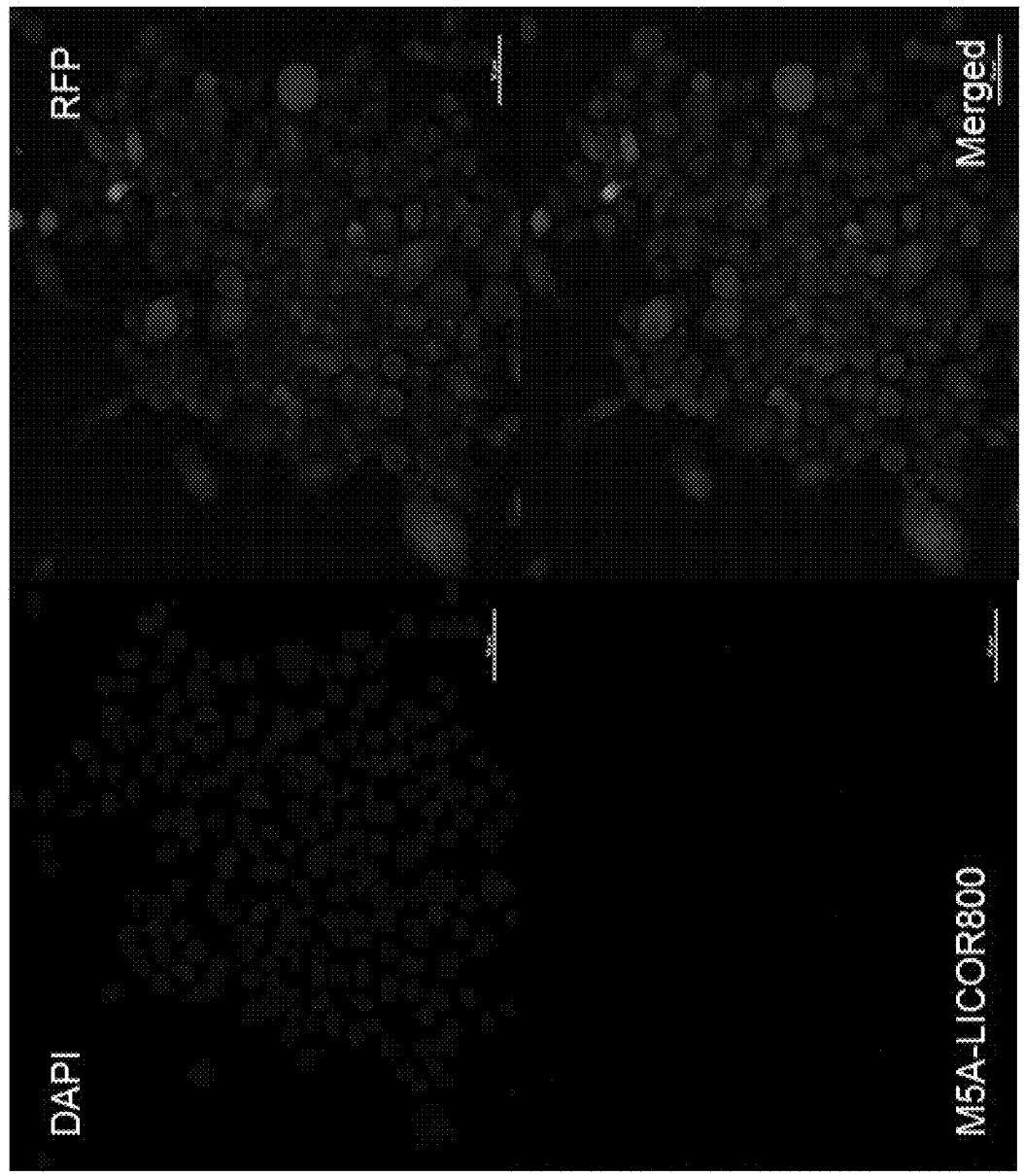

Staining with M5A-IRDye®800 showed that the fluorescent antibody bound the CEA-expressing BxPC-3-GFP human pancreatic cancer cell line (FIG. 5A). Merged images of the GFP and M5A-IRDye®800 channel show the fluorescent antibody localized at cell surfaces. Staining with M5A-IRDye®800 showed no fluorescent antibody binding to the CEA-negative MiaPaCa-2-RFP human pancreatic cancer cell line (FIG. 5B). Merged images of the RFP and M5A-IRDye®800 channel show an absence of antibody localization.

Figure 6A:
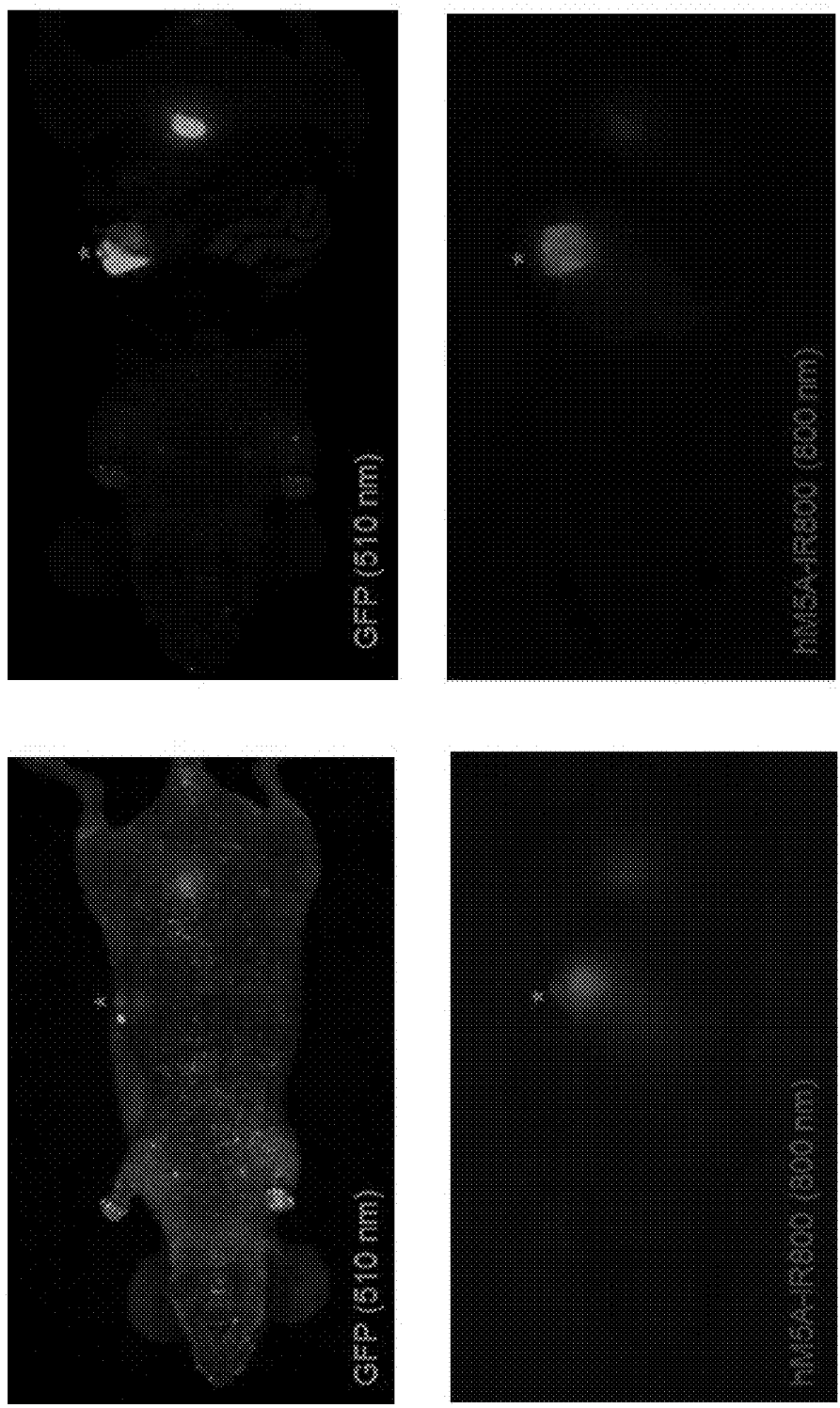
FIG. 6A shows selective tumor labeling of pancreatic cancer by M5A-IRDye®800. Non-invasive imaging of mice at 48 hours demonstrated a detectable fluorescence signal. Compared to GFP, the near-infrared wavelength demonstrated a stronger tumor signal through the tissue layers in non-invasive imaging (FIG. 6A, left hand panels) as well as the laparotomy view (FIG. 6A, right hand panels).
Figure 6B:
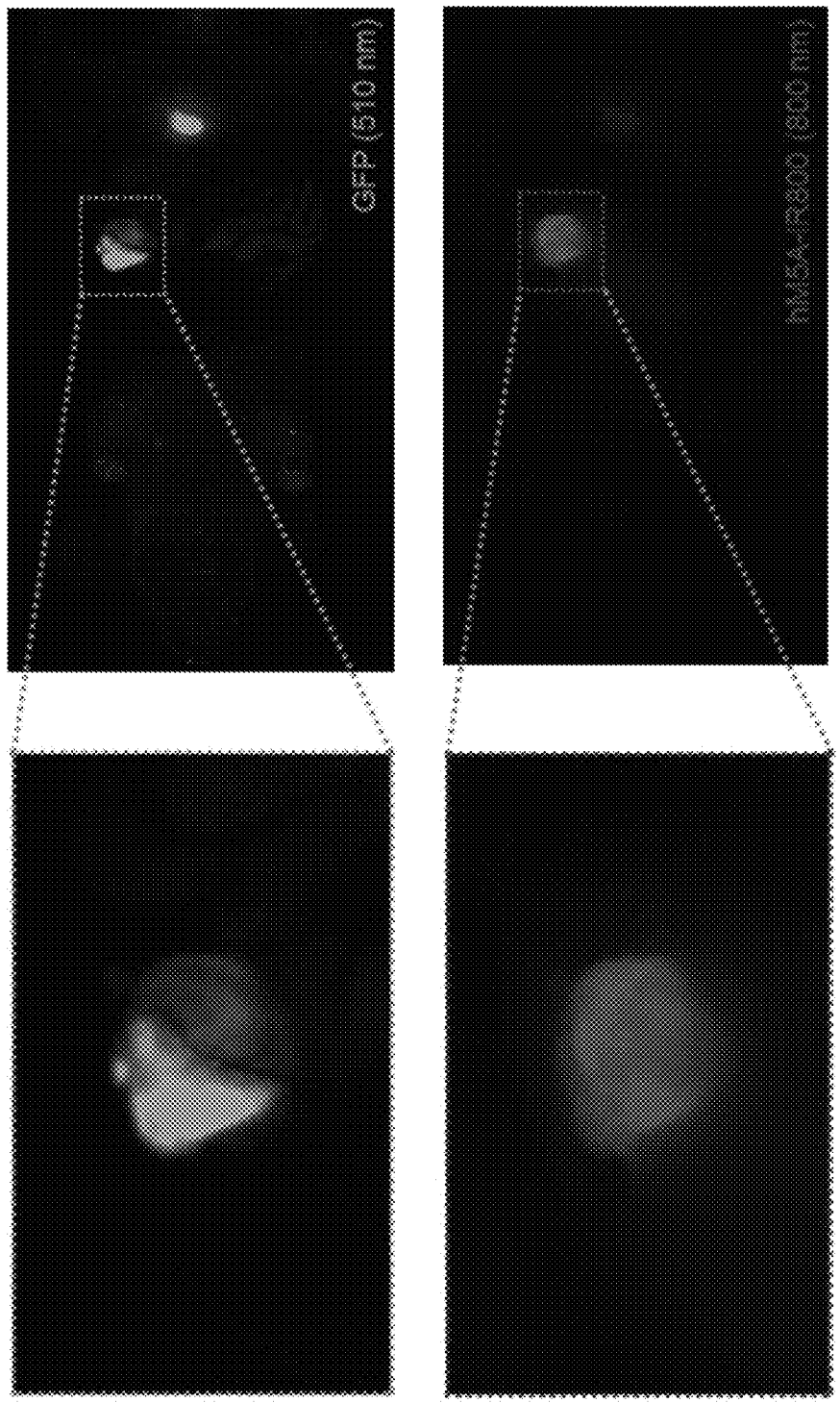
FIG. 6B shows improved tissue penetration with NIR wavelengths. The areas labeled by M5A-IRDye®800 clearly overlapped with the GFP tagged tumor. Magnified views show signal dampening due to overlying parenchyma and vascular in the GFP channel (FIG. 6B). The NIR wavelength showed superior tissue penetration.

Non-invasive imaging of mice at 48 hours showed that a fluorescence signal from the BxPC-3 pancreatic tumor was visible through the skin, abdominal wall soft tissue, and musculature (FIG. 6A: left panel, top and bottom images). When comparing the GFP and LICOR800 channels, the near-infrared wavelength demonstrates a stronger tumor signal through the tissue layers. In the same mouse, after laparotomy, the tumors are again visible in the GFP and LICOR-IRDye®800 channels (FIG. 6A: right panel, top and bottom images). The areas labeled by M5A-IRDye®800 clearly overlap with the GFP-tagged tumor. Magnified views show that the fluorescence signal from GFP can be dampened by the overlying pancreatic parenchyma and vasculature (FIG. 6B: top panels). In contrast, to the antibody-IR800 fluorescence was clearly detectable through overlying tissue (FIG. 6B: bottom panels). Importantly post-laparoscopy, FIG. 7 shows satellite CEA-positive metastatic lesions in the pancreatic tumor model.

To determine the pharmacokinetics of this antibody-dye conjugate, mice underwent intra-vital imaging at 6, 12, 24, 48, 72, and 96 hours after injection. The results are summarized in FIG. 8A. Peak fluorescence signal was obtained at 48 hours after initial injection. The mean fluorescence intensity value at 48 hours was 1695 counts compared to 6 hrs (1186 counts), 12 hrs (1204 counts), 24 hrs (1428 counts), 72 hrs (1046 counts), and 96 hrs (1022 counts). There was a high fluorescence signal in the liver from the earliest time point at 6 hours, but this signal rapidly decreased after 12 hours. The signal at the liver was the following: 6 hrs (1050 counts), 12 hrs (954 counts), 24 hrs (493 counts), 48 hrs (2269 counts), 72 hrs (111 counts), and 96 hrs (113 counts). There was also some mild background fluorescence signal at the skin and the highest signals were within the first 24-48 hours and the signal decreased steadily thereafter. The signal at the skin was as follows: 6 hrs (194 counts), 12 hrs (146 counts), 24 hrs (170 counts), 48 hrs (103 counts), 72 hrs (69 counts), and 96 hrs (85 counts).

Figure 8B:
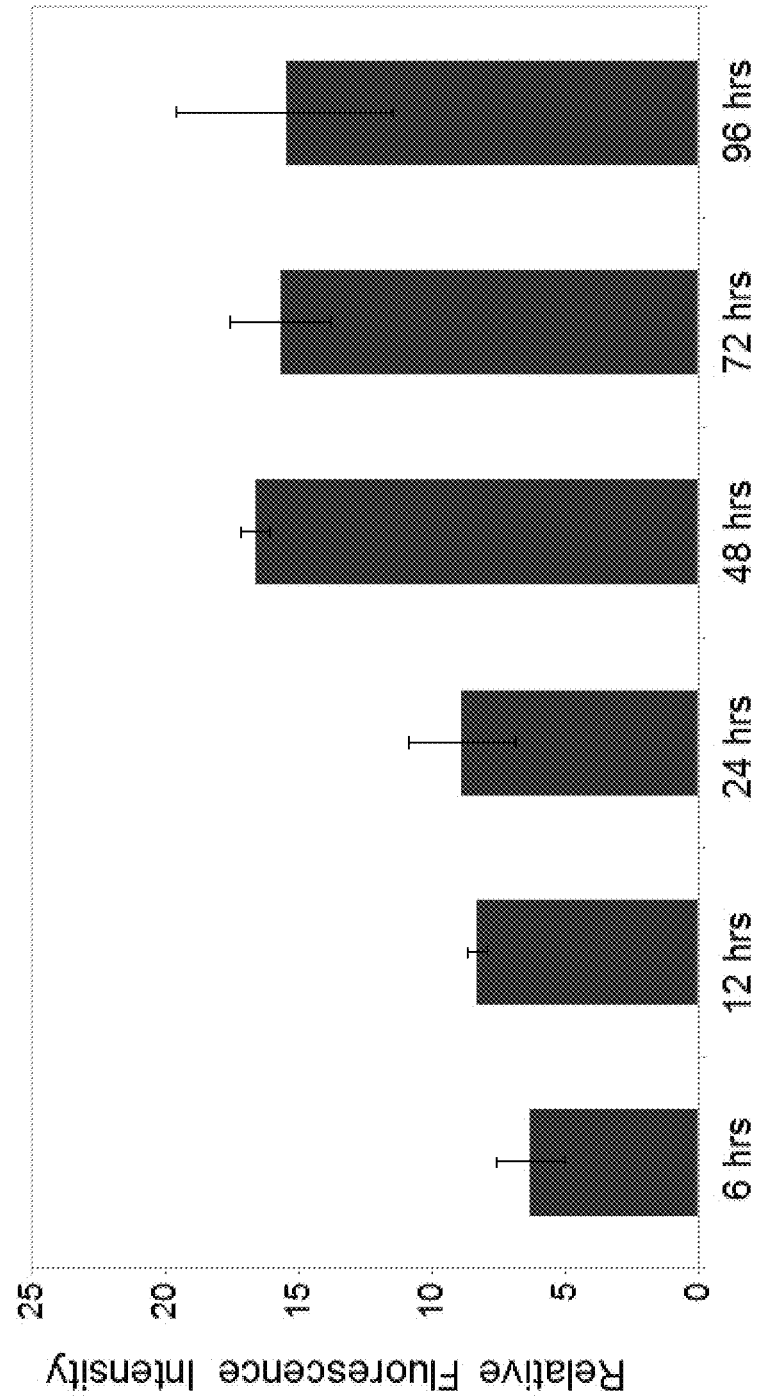
FIG. 8B shows M5A-IRDye®800 time course of tumor to background ratio. Tumor to background ratio of M5A-IRDye®800 at 6, 12, 24, 48, 72, and 96 hours after injection. The time of peak signal intensity correlated with the maximal tumor-to-background ratio at 48 hours (TBR=16.6).

The time of peak signal intensity correlated with the maximal TBR at 48 hours (TBR=16.6) as shown in FIG. 8B. There was a TBR greater than 5 at all time points: 6 hrs (TBR=6.3), 12 hrs (TBR=8.3), 24 hrs (TBR=8.8), 72 hrs (15.7), and 96 hrs (15.4).

Figure 9:
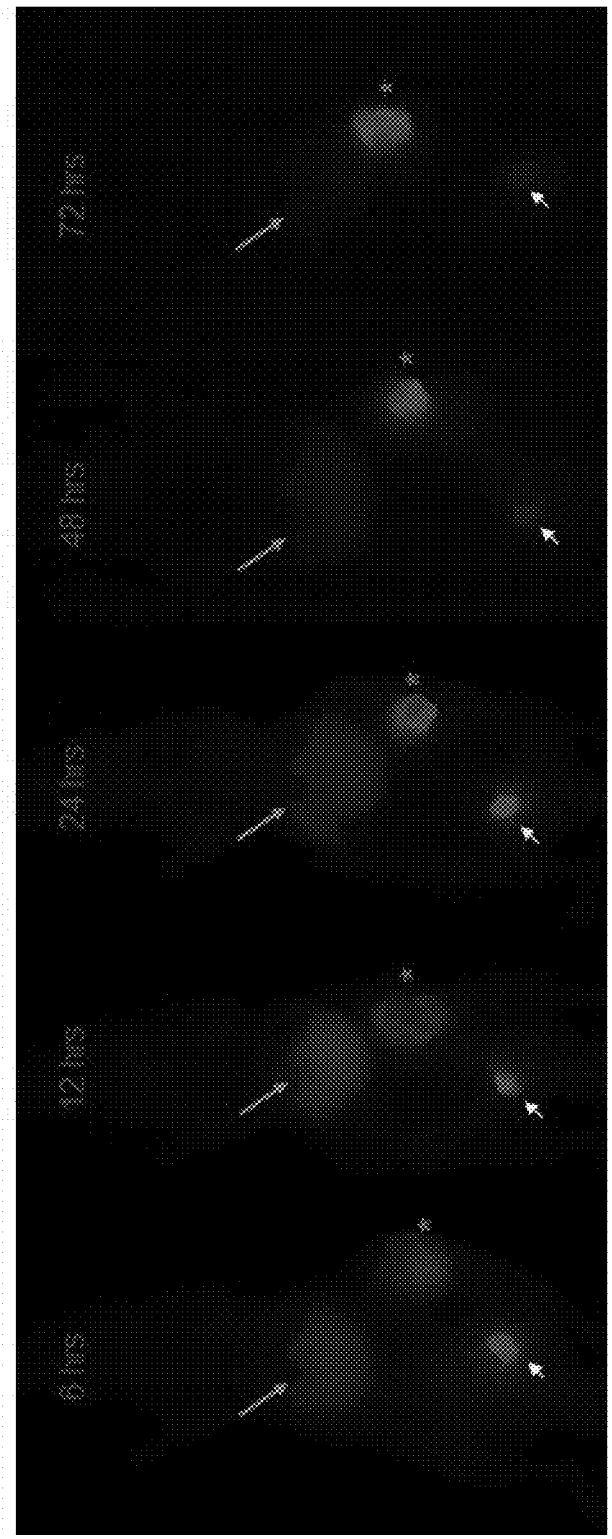
FIG. 9 shows M5A-IRDye®800 time course. Serial intravital images using M5A-IRDye®800 at 6, 12, 24, 48 and 72 hrs. All images demonstrate a fluorescent signal at the tumor at the IRDye®800 wavelength (blue asterisks). The images show additional background noise at the liver (green arrows) and bladder (yellow arrowhead) that steadily decreases over time.

Serial intra-vital images are displayed in FIG. 9. All images demonstrate a fluorescence signal at the tumor at the IR800 wavelength (blue asterisks). The images show additional background noise at the liver (green arrows) and bladder (yellow arrowheads) that steadily decreases over time.

Example 5: Blood Clearance of Various Conjugates

To further improve the imaging effects, various antibody-label conjugates were tested and compared for their blood clearance and normal tissue biodistribution in non-tumor bearing CEA Tg mice 073117. In this experiment, $^{125}$I-labeled M5A antibody, M5A-Intuitive IR800 conjugate, and M5A-LiCor IRDye®800 conjugate were injected into 3 mice per group and blood samples were taken at various time points. The blood clearance data was expressed as the percent injected dose per gram (% ID/g) vs. time in FIG. 10 (left). After the final time point, the mice were euthanized, necropsy performed, tissues counted for radioactivity and weight and the data expressed as % ID/g in FIG. 10 (right).

Figure 10:
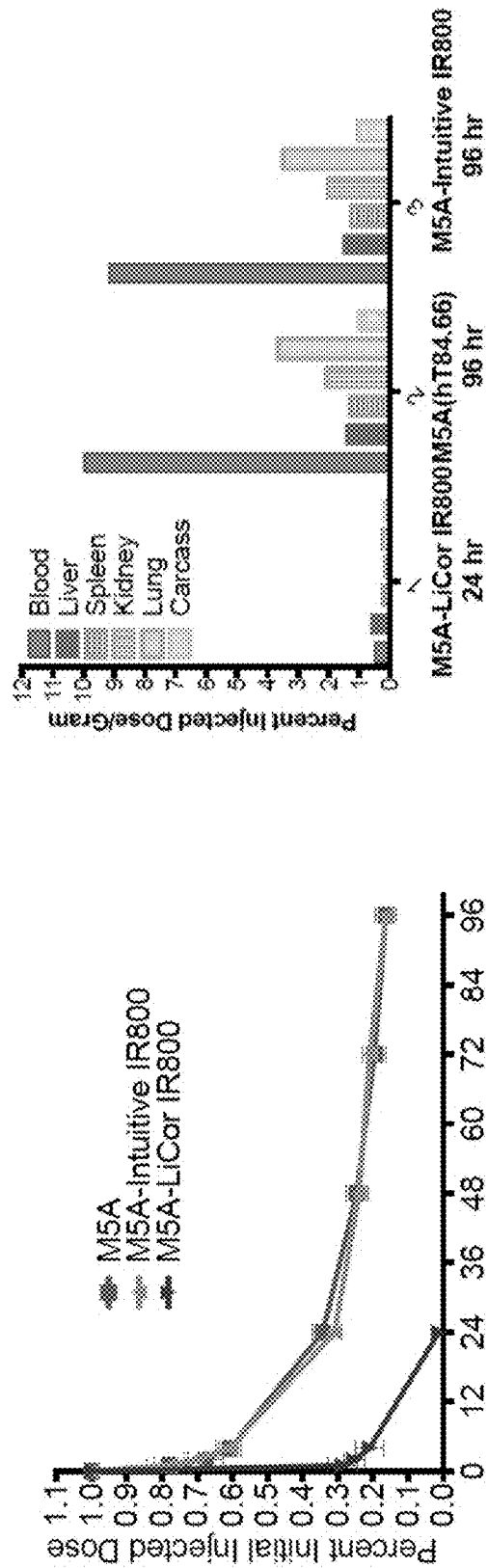
FIG. 10 shows blood clearance of $^{125}$I-labeled M5A antibody, M5A-Intuitive IR800 conjugate, and M5A-LiCor IRDye®800 conjugate in non-tumor bearing CEA Tg mice 073117.

As demonstrated in FIG. 10, the blood clearance profiles of $^{125}$I-labeled M5A antibody and M5A-Intuitive IR800 conjugate were almost identical, while M5A-LiCor IRDye®800 conjugate had a much faster clearance than the other two.

Figure 11:
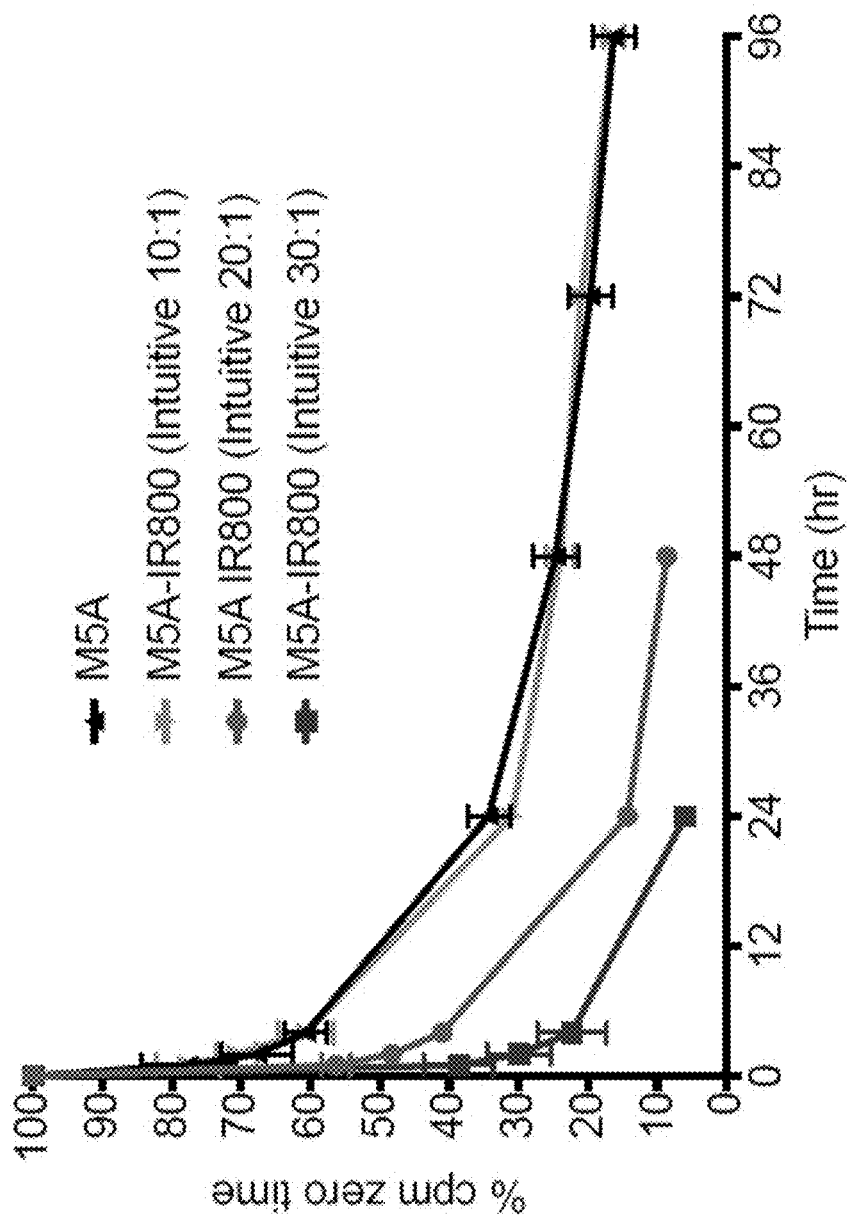
FIG. 11 shows the blood clearance time course of $^{125}$I-labeled M5A antibody and M5A-Intuitive IR800 conjugate at varying conjugation ratios in non-tumor bearing CEA Tg mice, expressed in starting molar ratios of antibody to dye in the conjugation reaction.

FIG. 11 shows the blood clearance of M5A-Intuitive IR800 conjugates with varying dye to antibody ratios. The data demonstrates faster blood clearance for higher fluorophore: antibody conjugation ratios in non-tumor bearing CEA Tg mice.

Figure 12:
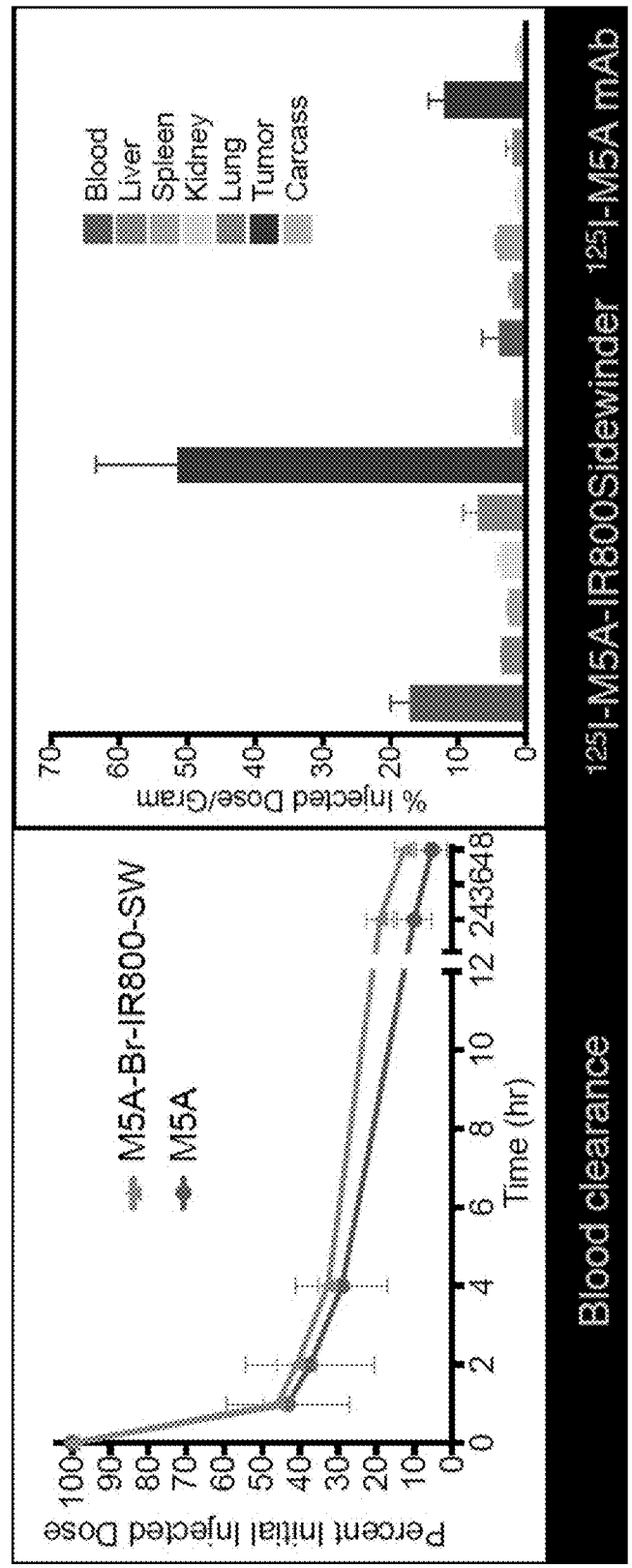
FIG. 12 shows the blood clearance time course of $^{125}$I-labeled M5A antibody and $^{125}$I-M5A-IR800Sidewinder conjugate in female athymic mice bearing human colorectal LS-174T.

FIG. 12 demonstrates that when a modified IR800 dye, PEG24 (IR800) PEG12-Br (Br-IR800-PEG sidewinder, received from Quanta Bioscience as a gift) was conjugated to M5A antibody, the blood clearance was comparable to or even better than the $^{125}$I-labeled M5A antibody.

Example 6: Comparison of the Imaging Effects of Intuitive IR800 and LiCor IRDye®800

M5A-Intuitive IR800 conjugate was tested and compared to M5A-LiCor IRDye®800 conjugate for their effects in non-invasive imaging. Athymic mice bearing human pancreatic cancer BxPC3-GFP tumor xenografts were injected with 75 micrograms of either M5A-LiCor-IRdye®800 or M5A-Intuitive-IR800 conjugated antibody.

FIGS. 13A-13D show the images in surgical orthotopic implant of BxPC3-GFP cells using 75 μg Intuitive dye, imaged at 72 hours after injection of the dye. FIG. 13A shows that Intuitive-IR800 signal presented through the skin when imaged non-invasively. FIG. 13B shows the white light post-laparotomy view showing the location of the tumor. FIG. 13C shows that the GFP signal from BxPC3-GFP tumors outlined the entire tumor. FIG. 13D shows that 800 nm signal from Intuitive-IR800 dye also outlined the entire tumor area.

Figure 14:
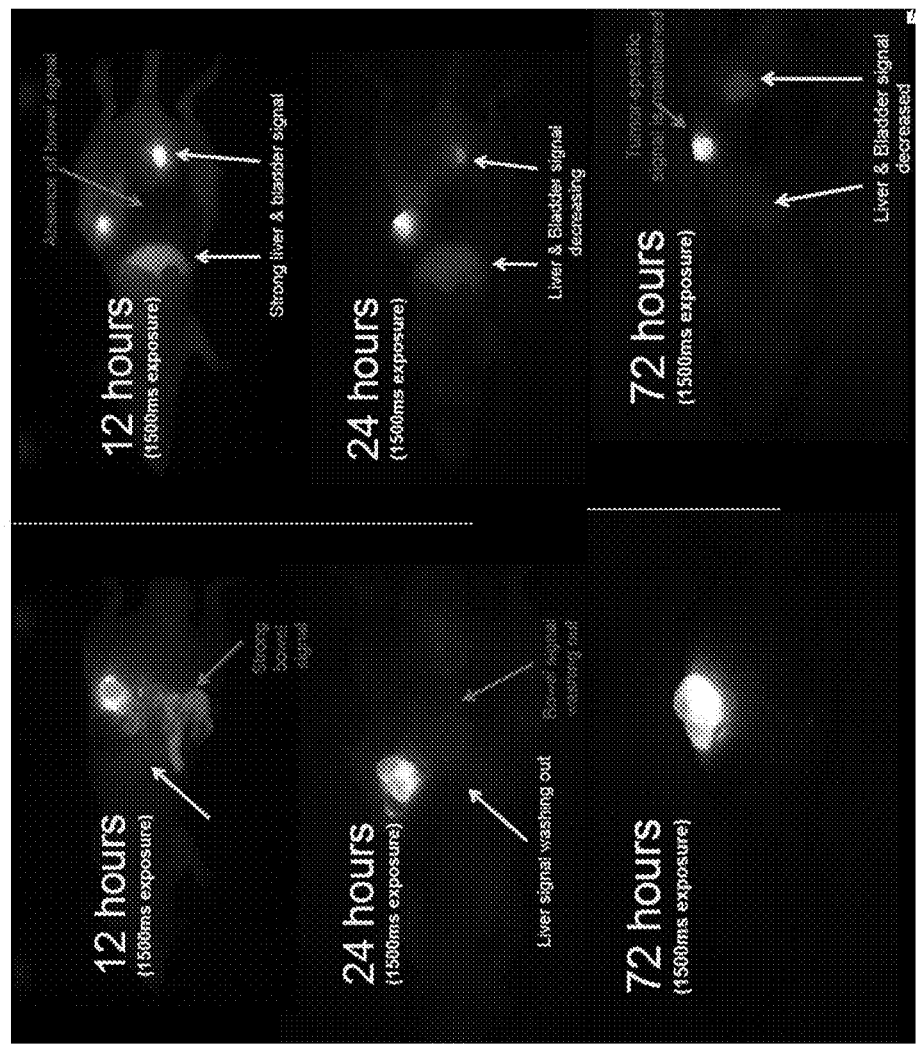
FIG. 14 shows comparison of Intuitive-IR800 signal (left panel) and LiCor IRDye®800 signal (right panel) at 12 hours, 24 hours, and 72 hours.
Figure 15:
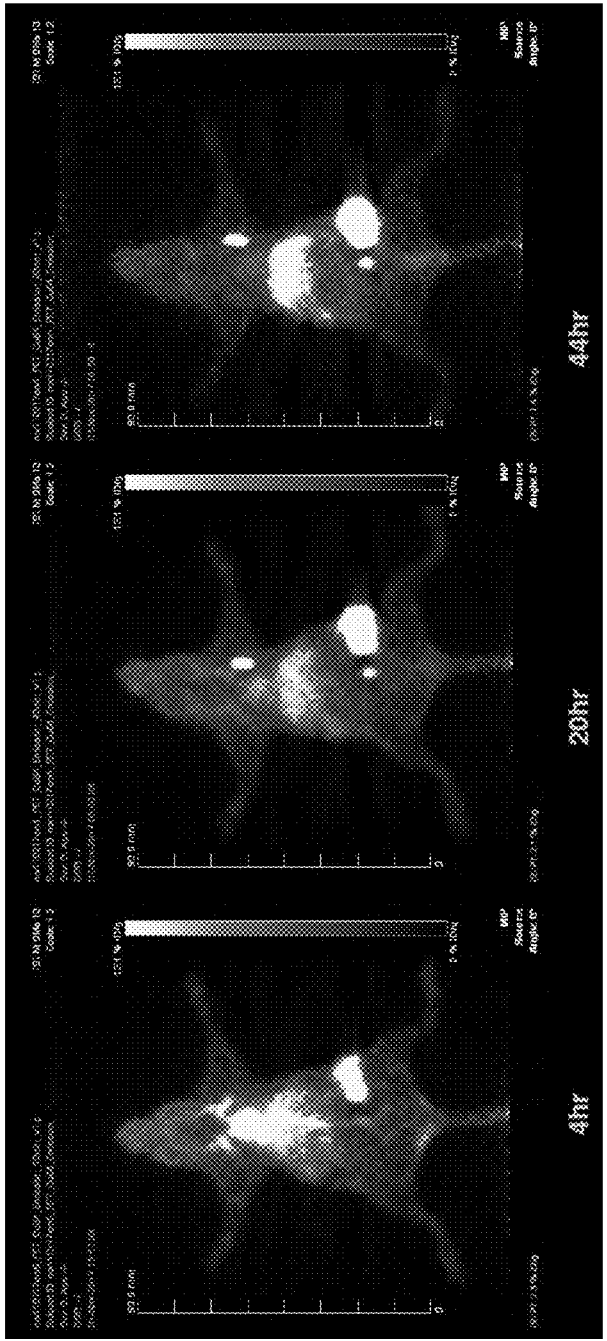
FIG. 15 shows serial PET imaging of the anti-CEA 64Cu-DOTA-M5A antibody in an athymic mouse bearing the human pancreatic cancer BxPC3-GFP xenograft.

FIG. 14 shows comparison of Intuitive-IR800 signal and LiCor IRDye®800 signal at 12 hours, 24 hours and 72 hours. Tumor-specific signal could be maintained for up to 72 hours when Intuitive-IR800 dye was used to conjugate M5A antibody.

Example 7: Tumor Imaging with Humanized Anti-CEA-64Cu-DOTA-M5A Antibody in a Pancreatic Cancer Model The PET imaging of the anti-CEA antibody was tested in a pancreatic cancer animal model. Briefly, the anti-CEA M5A antibody was conjugated with the metal chelate NHS-DOTA, the DOTA-M5A antibody was labeled with Cu-64 a PET radionuclide and purified by size exclusion chromatography. The $^{64}$Cu-DOTA-M5A antibody (100 microcuries) was injected into the tail vein of two athymic mouse bearing the human pancreatic cancer BxPC3-GFP xenograft. Serial PET images were taken at 4, 20 and 44 hours post-injection. The radioactive anti-CEA antibody PET imaging confirmed that the BxPC3 tumors were CEA positive as identified by M5A-IR800 optical imaging. Importantly, the PET images also identifies CEA positive lymph nodes which were confirmed by CEA immunohistochemistry.

As stated above, the foregoing are merely intended to illustrate the various embodiments of the present invention. As such, the specific modifications discussed above are not to be construed as limitations on the scope of the invention.

It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. DeLong J C, Hoffman R M, Bouvet M Current status and future perspectives of fluorescence-guided surgery for cancer. Expert Rev Anticancer Ther 2016:16:71-81.
2. Bouvet M, Hoffman R M Glowing tumors make for better detection and resection. Sci Transl Med 2011:3:110fs110.
3. Hiroshima Y, Lwin™, Murakami T, Mawy A A, Kuniya T, et al. Effective fluorescence-guided surgery of liver metastasis using a fluorescent anti-CEA antibody. J Surg Oncol 2016.
4. Hiroshima Y, Maawy A, Metildi C A, Zhang Y, Uehara F, et al. Successful fluorescence-guided surgery on human colon cancer patient-derived orthotopic xenograft mouse models using a fluorophore-conjugated anti-CEA antibody and a portable imaging system. J Laparoendosc Adv Surg Tech A 2014:24:241-247.
5. Metildi C A, Kaushal S, Luiken G A, Talamini M A, Hoffman R M, et al. Fluorescently labeled chimeric anti-CEA antibody improves detection and resection of human colon cancer in a patient-derived orthotopic xenograft (PDOX) nude mouse model. J Surg Oncol 2014: 109:451-458.
6. Kaushal S, McElroy M K, Luiken G A, Talamini M A, Moossa A R, et al. Fluorophore-conjugated anti-CEA antibody for the intraoperative imaging of pancreatic and colorectal cancer. J Gastrointest Surg 2008:12:1938-1950.
7. Metildi C A, Kaushal S, Pu M, Messer K A, Luiken G A, et al. Fluorescence-guided surgery with a fluorophore-conjugated antibody to carcinoembryonic antigen (CEA), that highlights the tumor, improves surgical resection and increases survival in orthotopic mouse models of human pancreatic cancer. Ann Surg Oncol 2014:21:1405-1411.
8. Metildi C A, Kaushal S, Snyder C S, Hoffman R M, Bouvet M Fluorescence-guided surgery of human colon cancer increases complete resection resulting in cures in an orthotopic nude mouse model. J Surg Res 2013:179: 87-93.
9. Rosenthal E L, Warram J M, de Boer E, Chung T K, Korb M L, et al. Safety and Tumor Specificity of Cetuximab-IRDye800 for Surgical Navigation in Head and Neck Cancer. Clin Cancer Res 2015:21:3658-3666.
10. Yazaki P J, Sherman M A, Shively J E, Ikle D, Williams L E, et al. Humanization of the anti-CEA T84.66 antibody based on crystal structure data. Protein Eng Des Sel 2004:17:481-489.
11. Boni L, David G, Mangano A, Dionigi G, Rausei S, et al. Clinical applications of indocyanine green (ICG) enhanced fluorescence in laparoscopic surgery. Surg Endosc 2015:29:2046-2055.
12. Namikawa T, Sato T, Hanazaki K Recent advances in near-infrared fluorescence-guided imaging surgery using indocyanine green. Surg Today 2015:45:1467-1474.
13. A V D S, Lin H, Henderson E R, Samkoe K S, Pogue B W Review of fluorescence guided surgery systems: identification of key performance capabilities beyond indocyanine green imaging. J Biomed Opt 2016:21:80901.
14. Yazaki P J, Lee B, Channappa D, Cheung C W, Crow D, et al. A series of anti-CEA/anti-DOTA bispecific antibody formats evaluated for pre-targeting: comparison of tumor uptake and blood clearance. Protein Eng Des Sel 2013: 26:187-193.
15. Maawy A A, Hiroshima Y, Zhang Y, Heim R, Makings L, Garcia-Guzman M, Luiken G A, Kobayashi H, Hoffman R M, Bouvet M. Near infra-red photoimmunotherapy with anti-CEA-IR700 results in extensive tumor lysis and a significant decrease in tumor burden in orthotopic mouse models of pancreatic cancer. PLOS One. 2015; 10: e0121989.
16. Metildi C A, Hoffman R M, Bouvet M. Fluorescence-guided surgery and fluorescence laparoscopy for gastrointestinal cancers in clinically-relevant mouse models. Gastroenterol Res Pract. 2013; 2013:290634.
17 Metildi C A, Kaushal S, Lee C, Hardamon C R, Snyder C S, Luiken G A, Talamini M A, Hoffman R M, Bouvet M. An LED light source and novel fluorophore combinations improve fluorescence laparoscopic detection of metastatic pancreatic cancer in orthotopic mouse models. J Am Coll Surg. 2012; 214:997-1007 e2.
18. Tran Cao H S, Kaushal S, Metildi C A, Menen R S, Lee C, Snyder C S, Messer K, Pu M, Luiken G A, Talamini M A, Hoffman R M, Bouvet M. Tumor-specific fluorescence antibody imaging enables accurate staging laparoscopy in an orthotopic model of pancreatic cancer. Hepatogastroenterology. 2012; 59:1994-9.
19. Wong J Y, Chu D Z, Williams L E, Liu A, Zhan J, Yamauchi D M, Wilczynski S, Wu A M, Yazaki P J, Shively J E, Leong L, Raubitschek A A. A phase I trial of (90) Y-DOTA-anti-CEA chimeric T84.66 (cT84.66) radioimmunotherapy in patients with metastatic CEA-producing malignancies. Cancer Biother Radiopharm. 2006; 21:88-100.
20. Yazaki P J, Shively L, Clark C, Cheung C W, Le W, Szpikowska B, Shively J E, Raubitschek A A, Wu A M. Mammalian expression and hollow fiber bioreactor production of recombinant anti-CEA diabody and minibody for clinical applications. J Immunol Methods. 2001; 253: 195-208.
21. Fluorescence-guided resection of experimental malignant glioma using cetuximab-IRDye 800CW. Warram J M, de Boer E, Korb M, Hartman Y, Kovar J, Markert J M, Gillespie G Y, Rosenthal E L. Br J Neurosurg. 2015 December; 29 (6): 850-8. doi: 10.3109/02688697.2015.1056090. PMID: 26073144
22. Strobel O, Hank T, Hinz U, Bergmann F, Schneider L, Springfeld C, et al. Pancreatic Cancer Surgery: The New R-status Counts. Ann Surg. 2017 March; 265 (3): 565-73.
23. Markov P, Satoi S, Kon M. Redefining the R1 resection in patients with pancreatic ductal adenocarcinoma. J Hepato-Biliary-Pancreat Sci. 2016 September; 23 (9): 523-32.
24. Fu X, Herrera H, Kubota T, Hoffman R M. Extensive liver metastasis from human colon cancer in nude and scid mice after orthotopic onplantation of histologically-intact human colon carcinoma tissue. Anticancer Res. 1992; 12: 1395e1397.
25. Fu X Y, Besterman J M, Monosov A, Hoffman R M. Models of human metastatic colon cancer in nude mice orthotopically constructed by using histologically intact patient specimens. Proc Natl Acad Sci USA. 1991; 88:9345e9349.
26. An Z, Jiang P, Wang X, Moossa A R, Hoffman R M. Development of a high metastatic orthotopic model of human renal cell carcinoma in nude mice: benefits of fragment implantation compared to cell-suspension injection. Clin Exp Metastasis. 1999; 17:265e270.

27. Fu X, Guadagni F, Hoffman R M. A metastatic nude-mouse model of human pancreatic cancer constructed orthotopically with histologically intact patient specimens. Proc Natl Acad Sci USA. 1992; 89:5645e5649.
28. Furukawa T, Fu X, Kubota T, Watanabe M, Kitajima M, Hoffman R M. Nude mouse metastatic models of human stomach cancer constructed using orthotopic implantation of histologically intact tissue. Cancer Res. 1993; 53:1204e1208.
29. Maawy A A, Hiroshima Y, Kaushal S, Luiken G A, Hoffman R M, Bouvet M. Comparison of a chimeric anti-carcinoembryonic antigen antibody conjugated with visible or near-infrared fluorescent dyes for imaging pancreatic cancer in orthotopic nude mouse models. J Biomed Opt. 2013; 18:126016.
30. Kitamura T, Sakuma S, Shimosato M, et al. Specificity of lectin-immobilized fluorescent nanospheres for colorectal tumors in a mouse model which better resembles the clinical disease. Contrast Media Mol Imaging. 2015; 10:135e143.
31. Hoffman R M, Yang M. Subcellular imaging in the live mouse. Nat Protoc. 2006; 1:775e782.
32. Girgis M D, Olafsen T, Kenanova V, McCabe K E, Wu A M, Tomlinson J S. Targeting CEA in Pancreas Cancer Xenografts with a Mutated scFv-Fc Antibody Fragment. EJNMMI Res. 2011 Nov. 7; 1 (1): 24.
33. Adams K E, Ke S, Kwon S, Liang F, Fan Z, Lu Y, et al. Comparison of visible and near-infrared wavelength-excitable fluorescent dyes for molecular imaging of cancer. J Biomed Opt. 2007 April; 12 (2): 024017.
34. Rosenthal E L, Moore L S, Tipirneni K, Boer E de, Stevens™, Hartman Y E, et al. Sensitivity and Specificity of Cetuximab-IRDye800CW to Identify Regional Metastatic Disease in Head and Neck Cancer. Clin Cancer Res. 2017 Aug. 15; 23 (16): 4744-52.
35. Zhu B, Sevick-Muraca E M. A review of performance of near-infrared fluorescence imaging devices used in clinical studies. Br J Radiol. 2015 January; 88 (1045): 20140547.
36. Moore L S, Rosenthal E L, Chung T K, Boer E de, Patel N, Prince A C, et al. Characterizing the utilities and limitations of repurposing an open-field optical imaging device for fluorescence-guided surgery in head and neck cancer patients. J Nucl Med. 2016 Sep. 1; jnumed.115.171413.
39. Maawy A A, Hiroshima Y, Zhang Y, Luiken G A, Hoffman R M, Bouvet M. Specific tumor labeling enhanced by polyethylene glycol linkage of near infrared dyes conjugated to a chimeric anti-carcinoembryonic antigen antibody in a nude mouse model of human pancreatic cancer. J Biomed Opt [Internet]. 2014 October [cited 2017 Jan. 23]; 19 (10). Available from: http://www.ncbi.nlm.nih.gov/pmc/articles/PMC4160999/

What is claimed is:

1. An antibody-fluorophore conjugate comprising a tumor-specific antibody conjugated to a PEG modified NIR fluorophore, wherein the antibody is an anti-TAG-72 antibody, wherein the NIR fluorophore is

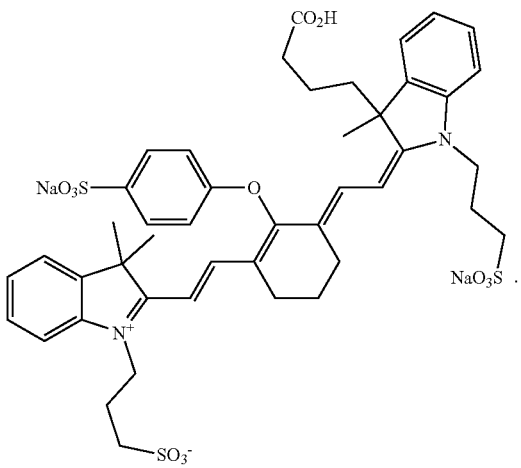

2. The conjugate of claim 1, wherein the anti-TAG-72 antibody is a humanized anti-TAG-72 antibody.
3. The conjugate of claim 2, wherein the humanized anti-TAG-72 antibody is a humanized anti-TAG-72 CC49 antibody.
4. The conjugate of claim 1, wherein the antibody is further labeled with a radioactive isotope.
5. The conjugate of claim 4, wherein the radioactive isotope is attached to the antibody via a chelating agent.
6. The conjugate of claim 5, wherein the chelating agent is DOTA.

* * * * *